United States Patent
Jones et al.

(10) Patent No.: US 10,882,961 B2
(45) Date of Patent: *Jan. 5, 2021

(54) METHOD OF PRODUCTION OF GRAFT CO-POLYMER EXCIPIENT WITH A SUPERIOR PEPTIDE AND PROTEIN BINDING PROPERTY

(71) Applicant: PharmaIN Corporation, Bothell, WA (US)

(72) Inventors: Cynthia C. Jones, Bothell, WA (US); Joshua F. Alfaro, Bothell, WA (US); Gerardo M. Castillo, Bothell, WA (US)

(73) Assignee: PharmaIN Corporation, Bothell, WA (US)

( * ) Notice: Subject to any disclaimer, the term of this patent is extended or adjusted under 35 U.S.C. 154(b) by 221 days.

This patent is subject to a terminal disclaimer.

(21) Appl. No.: 16/030,756

(22) Filed: Jul. 9, 2018

(65) Prior Publication Data

US 2018/0312642 A1 Nov. 1, 2018

Related U.S. Application Data

(62) Division of application No. 15/036,762, filed as application No. PCT/US2015/058885 on Nov. 3, 2015, now Pat. No. 10,035,885.

(60) Provisional application No. 62/074,356, filed on Nov. 3, 2014.

(51) Int. Cl.
| | |
|---|---|
| *C08G 81/00* | (2006.01) |
| *C08G 81/02* | (2006.01) |
| *C08G 69/10* | (2006.01) |
| *C08G 69/48* | (2006.01) |
| *A61K 47/34* | (2017.01) |
| *C08G 73/02* | (2006.01) |

(52) U.S. Cl.
CPC .............. *C08G 81/00* (2013.01); *A61K 47/34* (2013.01); *C08G 69/10* (2013.01); *C08G 69/48* (2013.01); *C08G 81/025* (2013.01); *C08G 73/02* (2013.01)

(58) Field of Classification Search
CPC .................... C08G 69/48; C08G 69/10; C08G 81/00–025; C08G 73/02–0293
See application file for complete search history.

(56) References Cited

U.S. PATENT DOCUMENTS

| | | |
|---|---|---|
| 2007/0141145 A1 | 6/2007 | Castillo et al. |
| 2007/0176892 A1 | 8/2007 | Tsui |
| 2009/0016892 A1 | 1/2009 | Yan |
| 2009/0053169 A1 | 2/2009 | Castillo et al. |
| 2009/0156459 A1 | 6/2009 | Castillo et al. |
| 2011/0044968 A1 | 2/2011 | Bolotin et al. |

FOREIGN PATENT DOCUMENTS

| | | |
|---|---|---|
| CN | 101365490 A | 2/2009 |
| WO | 2007/076371 A2 | 7/2007 |
| WO | 2009/089506 A1 | 7/2009 |
| WO | 2016/073518 A1 | 5/2016 |

OTHER PUBLICATIONS

Castillo, G.M., et al., "Extending Residence Time and Stability of Peptides by Protected Graft Copolymer (PGC) Excipient: GLP-1 Example," Pharmal Res (29):306-318, Aug. 2011.
Chinese Search Report dated May 28, 2019, issued in corresponding Chinese Application No. 201580067611.0, filed Nov. 3, 2015, 6 pages.
Castillo, G.M., et al., "Extending Residence Time and Stability of Peptides by Protected Graft Copolymer (PGC) Excipient: GLP-1 Example," Pharmaceutical Research 29(1):306-318, Jan. 2012.
International Search Report and Written Opinion dated Jan. 22, 2016, issued in corresponding International Application No. PCT/US15/058885, filed Nov. 3, 2015, 10 pages.
"NHS and Sulfo-NHS," Thermo Fisher Scientific Inc., 2009, 4 pages.
Y. Lapidot et al., "Use of Esters of N-Hydroxysuccinimide in the Synthesis of N-Acylamino Acids," Journal of Lipid Research 8:142-145, 1967.
Extended European Search Report dated Jun. 7, 2018, issued in corresponding European Patent Application No. 15857011.9, filed Nov. 3, 2015, 9 pages.

*Primary Examiner* — Ana L. Woodward
(74) *Attorney, Agent, or Firm* — Christensen O'Connor Johnson Kindness PLLC

(57) ABSTRACT

Provided herein is a process of preparing a semi-random graft co-polymer, the product of which is difficult to fully characterize chemically. The product of the present disclosure has unique and useful properties of 1) binding to a peptide and 2) upon co-administration of the product and the peptide into animals the product prolongs the blood circulation time and elevates the level of the peptide, compared to the peptide alone without the product of the disclosure.

16 Claims, No Drawings

Specification includes a Sequence Listing.

SEQUENCE LISTING

```
<160> NUMBER OF SEQ ID NOS: 3

<210> SEQ ID NO 1
<211> LENGTH: 28
<212> TYPE: PRT
<213> ORGANISM: Artificial Sequence
<220> FEATURE:
<223> OTHER INFORMATION: Synthetic

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 32
<212> TYPE: PRT
<213> ORGANISM: Artificial Sequence
<220> FEATURE:
<223> OTHER INFORMATION: Synthetic

<400> SEQUENCE: 2
```

```
Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
                20                  25                  30

<210> SEQ ID NO 3
<211> LENGTH: 31
<212> TYPE: PRT
<213> ORGANISM: Artificial Sequence
<220> FEATURE:
<223> OTHER INFORMATION: Synthetic

<400> SEQUENCE: 3

His Ala Glu Gly Thr Phe Thr Ser Asp Val Ser Ser Tyr Leu Glu Gly
1               5                   10                  15

Gln Ala Ala Lys Glu Phe Ile Ala Trp Leu Val Lys Gly Arg Gly
                20                  25                  30
```

METHOD OF PRODUCTION OF GRAFT CO-POLYMER EXCIPIENT WITH A SUPERIOR PEPTIDE AND PROTEIN BINDING PROPERTY

BACKGROUND

The development of new drug formulations for physiologically active peptides and proteins is focused on maintaining biological activity but even these are limited by the inherently short half-life or instability of the peptides and proteins in the body. This is especially true for small peptides and proteins with a hydrodynamic diameter of less than about 5 nm. There has long been a desire to alleviate such short half-life or instability of peptides and proteins in the body either by the use of infusion devices that constantly deliver rapidly degrading peptide or protein drugs or by providing an eroding depot of the drug under the skin. Development of excipients that can extend the half-life and/or provide stability of the peptides and proteins in the body and blood is a new area of research.

Liposomes that entrap unstable or short half-life drugs rely on the degradation of the liposome structure before the drug can be released. Polylactic-co-glycolic acid particles are another entrapment technology that relies on enzyme degradation of the polymer to release the drug. Semi-random grafting of two or more polymers that results in a co-polymer that binds rather than entraps the drug has been done (U.S. patent application Ser. Nos. 11/613,183, 11/971,482, and Castillo et al. Pharm. Res. 2012 Vol 29(1) p 306-318). Such co-polymers provide blood stability, extension of half-life, and prolonged elevated blood level of administered peptides and proteins (U.S. patent application Ser. Nos. 11/613,183, 11/971,482, and Castillo et al. Pharm. Res. 2012 Vol 29(1) p 306-318).

However, the ability to improve upon the manufacturing process and the potency of the grafted co-polymer product (the capacity to bind peptide on a per weight basis) is limited by the absence of technology that can determine the exact organization and periodicity, if any, in which the two polymers are grafted to the other polymer and relative to each other. It appears that there is a process-induced determinant of the organization of the components of the co-polymer molecule that then defines the final co-polymer product composition and properties. Because the compositional organization of the final product cannot be evaluated using the existing technology, the product can only be defined by the processes used to manufacture said product along with the product-associated properties that distinguishes said product from other products that are made using similar but not identical processes. Identification of such a process that makes a superior product is not obvious because of the lack of analytical technology that elucidates the atomic organization of the product and relying on the experimentation of various processes and evaluating the potency of the final product can take many years of detailed trial and error experimentation. The differences in composition of the final products can only be determined by their potency which can be defined by the process by which they are made. This is because the polymers are large, the co-polymerization reaction is random, and, as the reaction proceeds, the conformation of the polymers being grafted can change resulting in a non-random distribution that is determined by conformation at any given moment of the reaction timeline. The change in conformation is especially true with polylysine, which is known to change from alpha helix to random coil to beta sheet and vice versa depending on the environment (Arunkumar et al. 1997 Int. J. Biol. Macromol. 21(3):223-230). The conformation may also be influenced by other reagents (Mirtic and Grdadolnik 2013 Biophys. Chem. 175-176 p. 47-53) and potentially by catalysts. These influences can remain dynamic until the reaction terminates.

Some examples of previously synthesized polymers will be described below.

Example 6 of U.S. patent application Ser. No. 11/613,183 describes polylysine with 22% saturated with methoxypoly (ethylene glycol) (MPEG), by using MPEG succinimidyl-succinate or pre-activated N-hydroxysuccinimidyl polyethylene glycol (NHS-PEG) to saturate polylysine to 22%, which is materially different from the present disclosure (see below) that uses freshly activated MPEG-carboxyl using NHSS (N-hydroxysuccinimidesulfate) and EDC (1-ethyl-3-[3-dimethylaminopropyl]carbodiimide hydrochloride) to make solution B, which produces polylysine saturated to 50-60%. Additionally, Example 6 of U.S. patent application Ser. No. 11/613,183 modified 0.0228 mmol (20 mg) primary amino equivalent, or 0.104 mmol original primary amino based on 22% saturation of said product, by saturating the remaining primary amino with lauric acid after purification. The process of saturation used lauric acid equivalent to 2.4×mol of the original primary amino that was activated with NHSS equivalent to 1.1×mol of the original primary amino and EDC equivalent to 5×mol of the original primary amino. Therefore, Example 6 of U.S. patent application Ser. No. 11/613,183 is a completely different process compared to the present disclosure (see below) based on the reagents used and their ratios. The product is also a totally different product based on what can be measured analytically such as determination of primary amino groups using trinitrobenzenesulfonic acid (TNBS) giving only 22% PEG saturation.

Example 7 of U.S. patent application Ser. No. 11/613,183 describes polylysine with 22% saturated with MPEG by using MPEG succinimidyl-succinate or pre-activated NHS-PEG to saturate polylysine to 22% which is materially different from the present disclosure (see below) that uses freshly activated MPEG-carboxyl using NHSS and EDC (solution B) to produce polylysine saturated to 50-60%. Additionally, Example 7 of U.S. patent application Ser. No. 11/613,183 modified 0.0228 mmol (20 mg) primary amino equivalent, or 0.104 mmol original primary amino based on 22% saturation of said product, by saturating the remaining primary amino with stearic acid after purification. The process of saturation used stearic acid equivalent to 1.71× mol of the original primary amino that was activated with NHSS equivalent to 1.1×mol of the original primary amino and EDC equivalent to 5×mol of the original primary amino. Therefore, Example 7 of U.S. patent application Ser. No. 11/613,183 is a completely different process compared to the present disclosure (see below) based on the reagents used and their ratios. The product is also a totally different product based on what can be measured analytically such as TNBS giving only 22% PEG saturation.

Example 8 of U.S. patent application Ser. No. 11/613,183 describes polylysine with 22% saturated with MPEG by using MPEG succinimidyl-succinate or pre-activated NHS-PEG to saturate polylysine to 22%, which is materially different from the present disclosure (see below) that uses freshly activated MPEG-carboxyl using NHSS and EDC (solution B) to produce polylysine saturated to 50-60%. Additionally, Example 8 of U.S. patent application Ser. No. 11/613,183 modified 0.0228 mmol (20 mg) primary amino equivalent, or 0.104 mmol original primary amino based on 22% saturation of said product, by saturating the remaining primary amino with caprylic acid after purification. The process of saturation used caprylic acid equivalent to 3.36× mol of the original primary amino that was activated with NHSS equivalent to 1.1×mol of the original primary amino and EDC equivalent to 5×mol of the original primary amino. Therefore, Example 8 of U.S. patent application Ser. No. 11/613,183 is a completely different process compared to the present disclosure (see below) based on the reagents used and their ratios. The product is also a totally different product based on what can be measured analytically such as TNBS giving only 22% PEG saturation.

Example 9 of U.S. patent application Ser. No. 11/613,183 describes polylysine with 55% saturated with MPEG by using MPEG succinimidyl-succinate or pre-activated NHS-PEG to saturate polylysine to 55%, which is materially different from the present disclosure (see below) that uses freshly activated MPEG-carboxyl using NHSS and EDC (solution B) to produce polylysine saturated to 50-60%. Additionally, Example 9 of U.S. patent application Ser. No. 11/613,183 modified 0.0318 mmol (40 mg) primary amino equivalent of polylysine-polyethylene glycol (PLPEG), or 0.450 mmol original primary amino based on 55% saturation of said PLPEG product, by saturating the remaining primary amino of said PLPEG product with lauric acid after purification. The process of saturation used lauric acid equivalent to 1.8×mol of the original primary amino that was activated with NHSS equivalent to 0.34×mol of the original primary amino and EDC equivalent to 1.16×mol of the original primary amino. Therefore, Example 9 of U.S. patent application Ser. No. 11/613,183 is a completely different process compared to the present disclosure (see below) based on the reagents used and their ratios. The product is also a totally different product based on the presence of lauric acid or C12.

Example 12 of U.S. patent application Ser. No. 11/613, 183 used 1 g of Polylysine to make solution A. MPEG-succinate (5 g, 0.59×mol equivalent of the original primary amino) was activated for 18-20 min with 250 mg NHSS (1.15 mmol or 0.68×mol equivalent of the original primary amino) and EDC (2.6 mmol or 1.53×mol equivalent of the original primary amino) to make solution B. Solution C is made by mixing solutions A and B. After 4 hours a second solution B was prepared and added to solution C and the reaction was allowed to incubate overnight. This results in the saturation of epsilon primary amino group of polylysine to 55%. The final amounts of MPEG-succinate, NHSS, and EDC contained in solution C are 1.18×mol, 1.36×mol, and 3.06×mol equivalent of the original primary amino respectively. Compared to the present disclosure (see below) these steps of the process have different ratios and timing of reagent addition. The PLPEG product was purified, lyophilized, and the remaining primary amino groups were saturated with stearic acid by dissolving the purified PLPEG in 143 mL dichloromethane with 2 mmol triethylamine (0.76×mol equivalent of the original primary amino) and adding 2 mmol (0.76×mol equivalent of the original primary amino) of a freshly activated crude C18-NHS in dimethylformamide. The resulting product was purified and tested for GLP-1 binding and was found to have 33% free at 10% loading (see FIG. 37 of U.S. patent application Ser. No. 11/613,183). When the product of the present disclosure was loaded with GLP-1 at 10% loading no free GLP-1 was observed (see Table 61 below) indicating that the process outlined in Example 12 of U.S. patent application Ser. No. 11/613,183 produced a product that is different from the present disclosure.

In Example 13 of U.S. patent application Ser. No. 11/613, 183, the purified PLPEG (3 g) with 55% saturation of the primary amino groups used in Example 12 of U.S. patent application Ser. No. 11/613,183 was saturated with lignoceric acid using a process similar to Example 12 of U.S. patent application Ser. No. 11/613,183. Again, the process and the product of this process are different from the present disclosure based on the presence of lignoceric acid.

Examples 1-3 of U.S. patent application Ser. No. 11/971, 482 outline processes that use pre-activated NHS-PEG thus these are different processes than the present disclosure. In addition, Examples 1 and 3 have 27% and 22% saturation, respectively, and therefore the product is different from the process of the present disclosure. Example 2 has 55% saturation but is produced using NHS instead of NHSS, as in the present disclosure, so it is a different process and the product may have different PEG distribution along the polylysine backbone.

Examples 4-5 of U.S. patent application Ser. No. 11/971, 482 used 1 g of polylysine with 2.4 mmol primary amine to make solution A in 200 mM HEPES. MPEG-carboxyl (5 g, 0.42×mol equivalent of the original primary amino) was activated for 20 min with 250 mg NHSS (1.15 mmol or 0.48×mol equivalent of the original primary amino) and 500 mg EDC (2.6 mmol or 1.1×mol equivalent of the original primary amino) to make solution B. Activated solution B was added to solution A to make solution C. After 2 hours, a second solution B was prepared and added to solution C and the reaction was allowed to incubate overnight. This results in the saturation of epsilon primary amino groups of polylysine to 56%. The final amounts of MPEG-carboxyl, NHSS, and EDC contained in solution C are 0.84×mol, 0.96×mol, and 2.2×mol equivalent of the original primary amino respectively. Compared to the present disclosure (see below) these steps of the process have different solution C final ratios, in addition to different timing of reagent addition. The PLPEG product with 56% saturation was purified and portions were saturated with behenic acid and stearic acid as described below.

Example 5 of U.S. patent application Ser. No. 11/971,482 describes processes for behenic acid or C22 saturation, where PLPEG was made using a process different from the present disclosure (see below); PLPEG equivalent to 1.1 of original primary amine was dissolved in 53 mL dichloromethane with 200 μL or 1.44 mmol triethylamine (1.3× mol equivalent of the original primary amino) and 2.5 mmol (2.3×mol equivalent of the original primary amino) of freshly activated crude C22-NHS in 30 mL dimethylformamide:dichloromethane. This addition of C22 was repeated for a second time and allowed to react overnight and the product purified. This process is different from the present disclosure (see below) based on reagents used and their proportions, and results in a product with behenic acid which is different from the product of the present disclosure (see below).

Example 5 of U.S. application Ser. No. 11/971,482 describe processes for stearic acid or C18 saturation, PLPEG was made using a process different from the present disclosure (see below); PLPEG equivalent to 1.1 of original primary amine was dissolved in 53 mL dichloromethane with 200 μL or 1.44 mmol triethylamine (1.3×mol equivalent of the original primary amino) and 2.5 mmol (2.3×mol equivalent of the original primary amino) of freshly activated crude C18-NHS in 30 mL dimethylformamide:dichloromethane. This addition of C18 was repeated for a second time and allowed to react overnight and the product purified. This process is different from the present disclosure based on reagents used and their proportions. Functionally, when loaded with GLP-1 at 2% the product of this process gives 5% free peptide (see Table 1 of U.S. patent application Ser. No. 11/971,482 and Castillo et al. Pharm. Res. 2012 Vol 29(1) p 306-318) whereas the present disclosure at 2% loading gives 0% free peptide; in fact even at 5 and 10% loading the product of the present disclosure still shows 0% free indicating that the product of the present disclosure has a very high capacity for GLP-1 binding (see below). One is certain that the difference in properties or binding potency can only be explained by differences in composition.

Example 6 of U.S. patent application Ser. No. 11/971,482 used 1 g of polylysine with 2.4 mmol primary amine to make solution A in 200 mM HEPES. MPEG-succinate (5 g, 0.42×mol equivalent of the original primary amino) was activated for 20 min with 250 mg NHSS (1.15 mmol or 0.48×mol equivalent of the original primary amino) and 500 mg EDC (2.6 mmol or 1.1×mol equivalent of the original primary amino) to make solution B. Activated solution B was added to solution A to make solution C. After 2 hours a second solution B was prepared and added to solution C and the reaction was allowed to incubate overnight. This results in the saturation of epsilon primary amino group of polylysine to 57% with a hydrodynamic diameter of 14 nm. The final amounts of MPEG-carboxyl, NHSS, and EDC contained in solution C are 0.84×mol, 0.96×mol, and 2.2× mol equivalent of the original primary amino respectively. Compared to the present disclosure (see below) this process has different final proportions in solution C as well as different timing of reagent addition and thus the exact organization of PEG on the PL backbone must be different based on the properties of the final product after stearic acid saturation. The PLPEG product with 57% saturation was lyophilized and extracted four times with 50 mL dichloromethane and saturated with 2×2.5 mmol (2×mol equivalent of the original primary amino) C18-NHS dissolved in 30 mL of 1:2 vol/vol of dimethylformamide:dichloromethane after the addition of 400 µL or 2.88 mmol triethylamine (2.6×mol equivalent of the original primary amino). This product was made using a process that is different from the present disclosure (see below) and produces a product that has different potency (binding to GLP-1 at 2% loading has 5% free, see table 1 of U.S. patent application Ser. No. 11/971,482) compared to the product of the present disclosure (binding to GLP-1 at 2%, 5%, and 10% loading has 0% free). One is certain that the difference in properties can only be explained by differences in composition of the product.

Castillo et al. Pharm. Res. 2012 Vol 29(1) p 306-318 used 1 g polylysine with 2.6 mmol primary amino dissolved in 25 ml of 1 M HEPES, pH 7.4 to make solution A. Methoxy polyethylene glycol carboxymethyl (2 mmol or 0.77×mol equivalent of the original primary amino) was dissolved in 25 ml of 10 mM MES pH=4.7 with 4 mmol NHSS (1.54× mol equivalent of the original primary amino), and, once dissolved, EDC (6 mmol or 2.3×mol equivalent of the original primary amino) was added while stirring to make solution B. Activation was allowed to proceed for 20 min, and the activated MPEG-CM was added directly to the 20PL solution to make solution C. The pH of the solution was adjusted to 7.7 using NaOH and stirred for 2 h at room temperature. An aliquot was taken, and primary amino groups were measured by TNBS and found at 54% MPEG-CM saturation with hydrodynamic diameter of 14.4 nm. The crude PLPEG product was lyophilized and dissolved in ~100 ml dichloromethane and insoluble precipitates were removed and further extracted with ~50 ml dichloromethane. The supernatants were pooled, C18-NHS (1.4×mol equivalent of the original primary amino) in 20 mL dichloromethane was added to the pooled supernatant with magnetic stirring, then N,N-diisopropylethylamine (DIPEA, 2.3×mol equivalent of the original primary amino) was added and allowed to react for 4 h. Additional C18-NHS (3.6 mmol or 1.4×mol equivalent of the original primary amino; with total C18-NHS added of 2.8×mol equivalent of the original primary amino) was added and allowed to react overnight to obtain a crude co-polymer product which was purified by ultrafiltration after solvent change to ethanol-water. This process described by Castillo et al. in Pharm. Res. 2012 Vol 29(1) p 306-318 is different and has completely different ratios of reagents compared to the present disclosure. In addition, the resulting purified co-polymer product has different binding properties or potency (binding to GLP-1 at 2% loading has 5% free) compared to the product of the present disclosure (binding to GLP-1 at 2%, 5%, and 10% loading has 0% free; see Table 59) indicating a unique product composition.

SUMMARY

In one aspect, the present invention provides a process of preparing a semi-random graft co-polymer comprising the steps of:

(a) dissolving a linear polyamine backbone containing W amount of free primary amino groups in aqueous buffer with buffering range covering pH 7-8 and has a pH above 6.5 to obtain solution A having a volume Y;

(b) activating a polyethylene glycol (PEG) protective chain containing 0.5-1.2×W terminal carboxyl group by mixing it with 1.7-7.0×W of NHSS and 1.5-3.6×W of EDC in aqueous buffer, pH 4-5.5 to obtain solution B with a final volume of Z such that W/(Y+Z)=30-55 mM and allowing the activation to proceed for 0-30 min;

(c) mixing solution B with solution A resulting in solution C;

(d) adjusting the pH of solution C to above 6.5 if necessary;

(e) adding 0.5-1.5×W of additional EDC in small portions or all at once to solution C after 2-3 hours and waiting until the remaining primary amino is 55-40% of the original primary amino (45 to 60% saturation);

(f) increasing total volume of solution C when the remaining primary amino groups is 55-40% of the original primary amino by adding 1.0-2.5 volume equivalent (relative to solution C volume) of acetonitrile to obtain solution D and heating solution D to 40-70° C.;

(g) adding 0.5-6×W DIPEA or other tertiary amine to solution D;

(h) adding at least 0.75×W equivalent of C18-NHS in 40-70° C. acetonitrile to obtain solution E and stirring the solution at room temperature for at least 2 hours or until the remaining primary amino groups is less than 5% of the original primary amino to obtain the crude final product.

In another aspect, the present invention features a semi-random graft co-polymer obtainable by the methods described herein. The semi-random graft co-polymer can be mixed with a peptide selected from glucagon like peptide-1 and/or atrial natriuretic peptide, and derivatives thereof, to form a composition comprising non-covalent complex of semi-random graft co-polymer and peptide(s).

In yet another aspect, the present invention features a pharmaceutical composition including a semi-random graft copolymer obtainable by the methods described herein.

In another aspect, the present invention relates to a process of preparing a semi-random graft co-polymer, the product of which is difficult to fully characterize chemically. The product of the present invention has unique and useful properties of 1) binding to a peptide and 2) upon co-administration of the product and the peptide into animals the product prolongs the blood circulation time and elevates the level of the peptide, compared to the peptide alone without the product of the invention. The process that gives the product such properties cannot be duplicated by any other process that is significantly different from the process described in the present disclosure. Perhaps because of the confounding conformational changes of the backbone polymer as chemical reactions occurs in the process of the present disclosure, the graft co-polymer location along the backbone is heavily determined by the process. The resulting product cannot be chemically distinguished with certainty from the product produced using other processes without the challenge of developing new technology that can monitor the process and possible conformational changes that occur during the process. Such technology does not exist today. However, the product can be distinguished from the closest similar prior art product based on its properties of 1) its superior binding to a peptide and 2) its ability to impart to said peptide an elevated concentration level and prolonged blood circulation time upon administration into animals. The disclosure also relates to the product produced by such a process described in the present specification. This product-by-process being claimed in the present disclosure defines a product in terms of the process or method (manipulative steps) used to manufacture the same. The product and its known properties cannot be produced by any other known process to date, despite numerous experimentations and attempts to do so as are described below. The properties of the products of U.S. patent application Ser. No. 11/613,183 and U.S. patent application Ser. No. 11/971,482 were compared with those of the present disclosure. Although the products of U.S. patent application Ser. No. 11/613,183 and U.S. patent application Ser. No. 11/971,482 bind to the same peptide as the product of the present disclosure, the present product has much superior properties in both binding to the same peptide and imparting to said peptide an elevated level and prolonged blood circulation time upon administration into animals.

DETAILED DESCRIPTION

The present invention provides methods for preparing a semi-random graft co-polymer as described herein.

For example, the process of preparing a semi-random graft co-polymer often comprises the steps of: (a) dissolving a linear polyamine backbone containing W amount of free primary amino groups in aqueous buffer with buffering range covering pH 7-8 and has a pH above 6.5 to obtain solution A having a volume Y; (b) activating a polyethylene glycol (PEG) protective chain containing 0.5-1.2×W terminal carboxyl group by mixing it with 1.7-7.0×W of NHSS and 1.5-3.6×W of EDC in aqueous buffer, pH 4-5.5 to obtain solution B with a final volume of Z such that W/(Y+Z)=30-55 mM and allowing the activation to proceed for 0-30 min; (c) mixing solution B with solution A resulting in solution C; (d) adjusting the pH of solution C to above 6.5 if necessary; (e) adding 0.5-1.5×W of additional EDC in small portions or all at once to solution C after 2-3 hours and waiting until the remaining primary amino is 55-40% of the original primary amino (45 to 60% saturation); (f) increasing total volume of solution C when the remaining primary amino groups is 55-40% of the original primary amino by adding 1.0-2.5 volume equivalent (relative to solution C volume) of a polar organic solvent (e.g., acetonitrile) to obtain solution D and heating solution D to 40-70° C.; (g) adding 0.5-6×W DIPEA or other tertiary amine to solution D; (h) adding at least 0.75×W equivalent of C18-NHS in a polar organic solvent (e.g., acetonitrile) at 40-70° C. to obtain solution E and stirring the solution at room temperature for at least 2 hours or until the remaining primary amino groups is less than 5% of the original primary amino to obtain the crude final product.

The methods of the present invention comprise reaction of a linear polyamine backbone as described herein. The polyamine backbone comprises multiple primary amine groups as defined herein. The amounts of the different reagents to be used in the reactions of the polyamine backbone are quantified by reference to the total molar amount of amine groups on the polyamine backbone, as described herein. This total number of polyamine groups is denoted "W" and is given units of moles (mol).

As the skilled reader will appreciate, the amount of the reagents used in the methods described herein may be scaled according to the amount of primary amine groups in the polyamine backbone. Thus, the amount of the various reagents used in the processes as described herein are provided in terms of multiples of "W" as defined herein, and are expressed using the notation "Z×W", wherein Z is the factor by which W should be multiplied.

The processes of the invention are scalable. Thus, the skilled person will appreciate that the value of W is not particularly limited. Often, W will range from about 0.1 μmol to 1000 mol, more often W is from about 10 μmol to about 1 mol, still more often W is from about 100 μmol to about 100 mmol.

In the processes of the invention, the linear polyamine backbone is typically dissolved in aqueous buffer. The linear polyamine backbone is preferably polylysine as described herein.

The aqueous buffer is not particularly limited. The buffer may be any suitable buffer. Suitable buffers include, for example, PIPES (piperazine-N,N'-bis(2-ethanesulfonic acid)), BES ((N,N-bis [2-hydroxyethyl]-2-aminoethanesulfonic acid), MOPS ((N-morpholino)propanesulfonic acid), HEPES (defined herein), DIPSO (N,N-Bis(2-hydroxyethyl)-3-amino-2-hydroxypropanesulfonic acid), TEOA (defined herein), and the like. Particularly suitable buffers include HEPES and TEOA as defined below. Suitable buffers will typically buffer in the range pH 7-8. Typical concentrations of buffer salts in the buffer are from 50 to 250 mM, e.g. 100 mM. For example, the buffer may be 250 mM HEPES or 50 mM HEPES or 100 mM TEOA.

In step (a) of the process of the invention, the linear polyamine backbone is dissolved in aqueous buffer to obtain solution A. The volume of solution A is denoted "Y". The pH of solution A may be adjusted using standard techniques, such as addition of the acid or conjugate base of the buffer salt, to have a desired final pH. The final pH of solution A is typically greater than pH 6.5, such as from pH 6.5 to pH 9, e.g. from about pH 7 to about pH 8.

The process further comprises step (B1) or step (B2). Step B1 and Step B2 each comprise steps (b) to (d). In step B1 the process of the invention comprises formation of a solution B as described herein, which solution is added to solution A to form solution C. In step B2, the reagents that are used to form solution B in step B1 are added directly to solution A to form solution C, and solution B is not made. The following discussion applies unless otherwise stated to both steps B1 and steps B2.

In step (b) of the process of the invention, a protective chain is activated with EDC and NHSS (sulfo-NHS). The protective chain may be any suitable polymer as described herein. Typical polymers suitable for use as the protective chain include polyethylene glycol, polypropylene glycol and polyethylene-polypropylene glycol copolymer. The protective chain carries a carboxyl moiety at one end of the chain. The protective chain may or may not be alkoxylated, e.g. methoxylated or ethoxylated, at the other end of the chain. Preferred protective chains include methoxylated polyethyleneglycol (MPEG). The average molecular mass of the protective chain is not particularly limited. Often, the molecular mass of the protective chain is from 2 to 20 kDa, or from 4 to 12 kDa, or more often from 4 to 6 kDa. Typically, the average molecular mass is determined using gel permeation technology, as described herein.

Typically, the amount of protective chain used in step (b) corresponds to 0.5×W to 1.2×W terminal carboxyl groups; more often the amount of protective chain corresponds to 0.5×W to 1.1×W terminal carboxyl groups, still more often from 0.5×W to 1.0×W terminal carboxyl groups. For example, the amount of protective chain may be from 0.85×W to 0.95×W (e.g. 0.9×W), or from 0.75×W to 0.85×W (e.g. 0.8×W), or from 0.65×W to 0.75×W (e.g. 0.7×W), or from 0.55×W to 0.65×W (e.g. 0.6×W). Most typically, the amount of protective chain is from 0.8×W to 1×W, such as from 0.82×W to 0.95×W such as from 0.83×W to 0.93×W.

The protective chain is activated by reaction with EDC and NHSS.

Typically, the amount of EDC used is from 1.5×W to 3.6×W, such as from 1.5×W to 3.3×W, e.g. from 1.5×W to 3.0×W. For example, the amount of EDC used in step (b) may be from 2.5×W to 2.9×W (e.g. 2.7×W), or from 2.3×W to 2.6×W (e.g. 2.4×W), or from 2.0×W to 2.3×W (e.g. 2.1×W), or from 1.7×W to 2.0×W (e.g. 1.8×W). Most typically, the amount of EDC used is from 2.5×W to 2.9×W, such as from 2.5×W to 2.8×W.

Typically, the amount of NHSS used is from 1.7×W to 7.0×W, such as from 1.7×W to 4.0×W, e.g. from 1.7×W to 3.7×W, usually from 1.7×W to 3.4×W. For example, the amount of NHSS used in step (b) may be from 2.6×W to 3.2×W (e.g. 2.7×W), or from 2.3×W to 2.8×W (e.g. 2.4×W), or from 2.0×W to 2.5×W (e.g. 2.1×W), or from 1.7×W to 2.2×W (e.g. 1.8×W). Most typically, the amount of NHSS used is from 2.3×W to 2.8×W, such as from 2.5×W to 2.8×W.

Thus, for example, the amount of protective chain used may be 0.5-1.2×W, the amount of EDC may be 1.5-3.6×W and the amount of NHSS may be 1.7-7.0×W or 1.7-4.0×W. More typically, the amount of protective chain used may be 0.5-1.1×W, the amount of EDC may be 1.5-3.3×W and the amount of NHSS may be 1.7-3.7×W. Still more typically, the amount of protective chain used may be 0.5-1.0×W, the amount of EDC may be 1.5-3.0×W and the amount of NHSS may be 1.7-3.4×W. Most typically, the amount of protective chain may be from 0.8×W to 1×W, the amount of EDC may be from 2.5×W to 2.9×W and the amount of NHSS may be from 2.3×W to 2.8×W.

In step B1, the activation of the protective chain in step (b) of the process of the invention is conducted in aqueous buffer to yield solution B. The buffer which may be used is not particularly limited, and any suitable buffer can be used. Suitable buffers will typically buffer in the range pH 4-5.5. A suitable buffer system can include, for example, MES (2-(N-morpholino)ethanesulfonic acid). The pH of the solution is usually from 4.0 to 5.5, e.g. from pH 4.2 to pH 5.2, such as from pH 4.4 to pH 5.0, e.g. from 4.5 to 4.9. Typical concentrations of buffer salts in the buffer are from 1 to 100 mM, e.g., 10 mM. For example, the buffer may be 10 mM MES buffer, pH 4.7.

The volume of the activated protective chain in the aqueous buffer solution is denoted as volume Z. Volume Z is typically such that W/(Y+Z) is from about 30 mM to about 55 mM, e.g. from about 40 mM to about 50 mM, such as about 45 mM. Volumes Y and Z are typically given in the same units. For example, both Y and Z are typically given in units of litres (L). The skilled person will understand that the term "litres" includes standard variants such as μL ($10^{-6}$ L), mL ($10^{-3}$ L), cL ($10^{-2}$ L) and the like.

The reaction time for the activation process is typically less than 30 minutes, such as from 0 to 30 min, e.g. from 2 to 25 mins, often from 10 to 24 mins, such as from 18 to 22 mins, e.g. about 20 mins.

In step (c) of the process of the invention, solution A as described herein is mixed with solution B or with the reagents comprised therein as described herein to obtain solution C. Reagents are often added under vigorous stirring in such a way that avoids precipitation. Usually, continuous stirring is used to agitate the solutions. Continuous stirring may be achieved by any suitable technique, such as by a magnetic stirrer or mixer or by manual stirring e.g. with a stirring rod. Typical stirring (rotation) speeds are from 50 to 2000 rpm (e.g. from 200 to 1500 rpm). Vigorous stirring is often required to avoid precipitation (as described herein), and elevated rotation speeds are often used, such as from 500 to 2000 rpm (e.g. from 1000 to 2000 rpm). Reagents and solutions are typically added slowly such as from 0 to 50 mL/min, more typically from 0 to 20 ml/min (e.g., from 0 to 10 mL/min). Slow addition of solutions can be achieved using standard techniques such as a dropping pipette or a peristaltic pump. Other suitable methods will be known to those skilled in the art. Slow addition of solid reagents is achieved by addition of a portion of the total reagent to be added in any step, with time (such as from 10 s to 10 min) allowed to elapse before addition of the next portion. Alternatively, a gradual feed of solid reagents can be achieved using, for example, a funnel or other standard techniques familiar to those skilled in the art.

Step (d) of the process of the invention is optional, and may be present or absent. When present, step (d) corresponds to adjusting the pH of solution C using standard techniques, such as addition of the acid or conjugate base of the buffer salt, to have a desired final pH. The final pH of solution C is typically greater than pH 6.5, such as from pH 6.5 to pH 9, e.g. from about pH 7 to about pH 8.

In step (e) of the present invention, additional EDC is added to solution C. The manner in which the additional EDC is added is not particularly limited. For example, the additional EDC may be added in one administration, or multiple aliquots of EDC may be added separately until the final desired amount of EDC has been added to solution C. Thus, the additional EDC may be added in one or more portions. The additional EDC is typically not added to solution C immediately after the formation of solution C; rather, solution C is often allowed to react for 2 to 3 hours, such as about 2.5 hours (e.g., about 2 hours) after its formation as described herein before the additional EDC is added.

Typically, from 0.5×W to 1.5×W of additional EDC is added to solution C, more typically from 0.5×W to 1.2×W additional EDC is added, still more typically from 0.5×W to 1.1×W, such as from 0.5×W to 1.0×W additional EDC is added. For example, the amount of additional EDC added may be from 0.85×W to 0.95×W (e.g. 0.9×W), or from 0.75×W to 0.85×W (e.g. 0.8×W), or from 0.65×W to 0.75×W (e.g. 0.7×W), or from 0.55×W to 0.65×W (e.g. 0.6×W). Thus, the total amount of EDC in solution C in moles is typically from 2×W to 5.1×W, more typically from 2×W to 4.8×W, more typically from 2×W to 4.4×W, still more typically from 2×W to 4×W, such as from 3×W to 3.9×W, e.g. from about 3.4×W to about 3.8×W.

Once the additional EDC has been added, sufficient time is typically allowed before proceeding to any further reaction steps that may be required for the amount of remaining primary amino groups on the linear polyamine backbone to be from 55-40% of the original primary amino (45 to 60% saturation). It is generally undesirable to freeze or lyophilize solution C either before the additional EDC is added or shortly after additional EDC is added. However, solution C may be frozen or lyophilized after additional EDC has been added and the remaining primary amino groups on the linear polyamine backbone is from 55-40% of the original primary amino (45 to 60% saturation). Thus, it is preferable that solution C is not lyophilized or frozen before the additional EDC is added or after additional EDC is added until the remaining primary amino groups on the linear polyamine backbone is from 55-40% of the original primary amino (45 to 60% saturation).

The present invention also provides a method comprising steps (a) to (e) as described herein and further comprising steps (f) to (h) as described herein.

Step (f), when present, includes obtaining solution D from solution C as described herein. Step (f) may comprise:
i) freezing and lyophilizing solution C wherein the remaining primary amino groups are 55-40% of the original primary amino (i.e., the solution obtained from step (e) as described herein) and reconstituting the lyophilized material in organic solvent(s) to obtain solution D; or
ii) adding at least W of a strong nucleophile (such as hydroxyl amine) to solution C wherein the remaining primary amino groups are 55-40% of the original primary amino (i.e., the solution obtained from step (e) as described herein) and purifying the product by ultrafiltration, followed by lyophilization and dissolving the product in organic solvent(s) to obtain solution D; or
iii) increasing the total volume of solution C wherein the remaining primary amino groups are 55-40% of the original primary amino (i.e., the solution obtained from step (c) as described herein) by adding 1.0-2.5 volume equivalents of organic solvent(s) to obtain solution D and heating solution D to 40-70° C., inclusive, for at least 10 minutes and adding a strong nucleophile then purifying the product by ultrafiltration and lyophilization; then reconstituting solution D with pure PLPEG product in organic solvent(s) or
iv) increasing total volume of solution C wherein the remaining primary amino groups are 55-40% of the original primary amino (i.e., the solution obtained from step (e) as described herein) by adding 1.0-2.5 volume equivalent of organic solvent(s) to obtain solution D and heating solution D to 40-70° C., inclusive;

Suitable organic solvents include acetonitrile, acetone, dichloromethane, dimethylformamide, dimethyl sulfoxide and 1-methyl-2-pyrrolidinone, with acetonitrile being particularly suitable. Acetonitrile as a solvent may be diluted in water or other suitable solvents to a final concentration of less than 100% acetonitrile, for example from 10% to 90% acetonitrile, such as from 30% to 70% acetonitrile, typically from 50% to 70% acetonitrile such as from 60% to 70% acetonitrile, e.g., about 66% acetonitrile (i.e.: 66% acetonitrile in water) is often used. In some embodiments, acetonitrile can be diluted in water to a final concentration of 64%.

When step (f) is according to option (i), suitable organic solvents include acetonitrile, acetone, dichloromethane, dimethylformamide, dimethyl sulfoxide, and 1-methyl-2-pyrrolidinone, with acetonitrile being particularly suitable. The amount of solvent to be used in reconstituting the lyophilized material to obtain solution D may be readily determined by the skilled person. Often, the amount of solvent into which the lyophilized material is reconstituted is 1.0 to 2.5 volume equivalents of the volume of the solution C wherein the remaining primary amino groups are 55-40% of the original primary amino (i.e., the solution obtained from step (e) as described herein).

When step (f) is according to option (ii), the strong nucleophile used is not particularly limited, and, for example, may include any strong nucleophile as described herein. Particularly suitable strong nucleophiles include $NH_2OH$, NaOR, LiR, NaOH or KOH, NaCN or KCN, NaCCR (acetylide anion), $NaNH_2$, NaNHR, $NaNR_2$, NaI, LiBr, KI, and $NaN_3$. In some embodiments, R is a $C_1$-$C_6$ alkyl group or a $C_2$-$C_6$ alkenyl group as defined herein. When step (f) is according to option (ii), ultrafiltration can be conducted as described herein. Often, the amount of acetonitrile into which the lyophilized material is reconstituted is 1.0 to 2.5 volume equivalents of the volume of the solution C wherein the remaining primary amino groups are 55-40% of the original primary amino (i.e., the solution obtained from step (e) as described herein).

When step (f) is according to option (iii), the solution D obtained therein is typically heated to from 40 to 70° C., such as from 50 to 65° C., e.g. from 55 to 60° C. Heating is typically conducted for 10-60 minutes, such as from 10 to 30 minutes, e.g. 10-20 minutes. The strong nucleophile is not particularly limited, and, for example, may include any strong nucleophile as described herein, such as the strong nucleophiles described for option (ii) of step (f) above. The amount of acetonitrile to be used in reconstituting solution D may be readily determined by the skilled person. Often, the amount of acetonitrile into which the lyophilized material is reconstituted is 1.0 to 2.5 volume equivalents of the volume of the solution C wherein the remaining primary amino groups are 55-40% of the original primary amino (i.e., the solution obtained from step (e) as described herein). For the avoidance of doubt, when step (f) is according to option (iii), the term PLPEG product refers to the product of the lyophilizaton step.

When step (f) is according to option (iv), the solution D obtained therein is typically heated to from 40-70° C., such as from 50 to 65° C., e.g. from 55 to 60° C. Heating is typically conducted for 10 to 60 minutes, such as from 10 to 30 minutes, e.g. 10 to 20 minutes.

Step (g) when present comprises adding 0.5-6×W tertiary amine to solution D. Any suitable tertiary amine can be used, such as trimethylamine (TEA), N,N-diisopropylethylamine (DIPEA), and triphenylamine. DIPEA is particularly suitable.

Step (h) when present comprises adding at least 0.75×W equivalent of long chain fatty acid-NHS in 40-70° C. acetonitrile, acetone, dichloromethane, dimethylformamide, dimethyl sulfoxide, and/or 1-methyl-2-pyrrolidinone to the product of step (g) to obtain solution E, and stirring the solution at room temperature for at least 2 hours or until the remaining primary amino groups are less than 5% of the original primary amino to obtain the crude final product.

Typically, from 0.75×W to 2×W equivalents of long chain fatty acid-NHS is added, more typically from 0.8×W to 1.5×W is added, still more typically from 0.85×W to 1.2×W is added, such as from about 0.9×W to about 1.1×W, e.g. about 1×W equivalent of long chain fatty acid-NHS may be added.

The long chain fatty acid-NHS may be any suitable long chain fatty acid in which the carboxyl group is esterified with NHS. Suitable long chain fatty acids are described herein, and include those with aliphatic tails comprising from 13 to 21 carbon atoms. Examples of long chain fatty acids which may be esterified with NHS to yield long chain fatty acid-NHS groups suitable for use in this process include those described herein.

The long chain fatty acid-NHS is added to the product of step (g) in an organic solvent such as a polar organic solvent, e.g. acetonitrile. The organic solvent is typically at 40-70° C., such as from 50 to 65° C., e.g. from 55 to 60° C. The fatylation reaction is allowed to proceed for at least 2 hours, e.g. from 2 to 24 hours, such as from 2 hours to 12 hours, e.g. from 6 to 12 hours. The reaction proceeds until the remaining primary amino groups are less than 5% of the original primary amino, thus yielding the crude final product.

The final crude product as described herein can be purified and isolated using standard techniques. For example, remaining organic solvent and/or excess fatty acids in the final product can be extracted using a solvent such as ethyl acetate. Typically said extraction is conducted more than once, such as two or more times. The extracted product can then be purified by ultrafiltration. In some embodiments, the final crude product can be purified by exchanging the organic solvent into water and washing the final product by ultrafiltration using typically at least 10 volume changes of ethanol and water. The final product can be frozen and/or can be lyophilized.

In one aspect of the invention, solution B in step "b" has 0.5-1.2×W carboxyl group; 1.7-6.0×W of NHSS; and 1.5-3.6×W of EDC.

In another aspect of the invention, solution B in step "b" has 0.5-1.2×W carboxyl group; 1.7-5.0×W of NHSS; and 1.5-3.6×W of EDC.

In another aspect of the invention, solution B in step "b" has 0.5-1.2×W carboxyl group; 1.7-4.0×W of NHSS; and 1.5-3.6×W of EDC.

Table 1 below shows typical relationships of the reagents to each other irrespective of the scale of the process. Table 1 refers as exemplary aspects of the invention in steps (f), (g) and (h) to acetonitrile, DIPEA and C18-NHS, respectively; however, the skilled person will appreciate that these components are given by way of example and that the invention is not limited to these components, with other appropriate components as described herein. Similar comments apply to Tables 2 to 12 below.

TABLE 1

| Step | | Amount/value | Volume of solution |
|---|---|---|---|
| a | Polyamine primary amino in solution A (moles) | W | Y |
| b | Protective chain carboxyl in solution B (moles) | 0.5-1.2 × W | Z |
| b | NHSS in solution B (moles) | 1.7-7.0 × W | Z |
| b | EDC in solution B (moles) | 1.5-3.6 × W | Z |
| b | pH of solution B | 4.0-5.5 | Z |
| b | Activation time (min) | 0-30 | Z |
| c & d | pH of solution C | above 6.5 | |
| c & d | Primary amino in solution C (Molar) | W/(Y + Z) = 30-55 mM | |
| e | Additional EDC added to solution C until primary amine is 45 to 60% saturated [total EDC in C] (moles) | 0.5-1.5 × W [2.0-5.1 × W] | |
| f | Acetonitrile in solution D | 1.0-2.5 × vol. of solution C | |
| g | DIPEA or other tertiary amine in solution D (moles) | 0.5-6 × W | |
| h | C18-NHS in solution E (moles) | At least 0.75 × W | Sol D volume + 3° amine + C18-NHS volume |

Often, the linear polyamine backbone is polylysine having a degree of polymerization of 35-150 based on light scattering or nuclear magnetic resonance (NMR) analysis. Usually, the linear polyamine backbone is polylysine with degree of polymerization of 35-85 based on light scattering or nuclear magnetic resonance (NMR) analysis.

Typically, the PEG protective chain is methoxy PEG (MPEG) having a single carboxyl terminus and has 4-12 kDa number average molecular weight or Mn based on Gel Permeation Chromatography (GPC). Often, the PEG protective chain is methoxy PEG chain with a single carboxyl terminus and has 4-6 kDa number average molecular weight or Mn based on Gel Permeation Chromatography (GPC).

In another aspect of the present invention, the above aforementioned process is such wherein in step "e", 0.5-1.2×W of EDC is added to solution C; wherein in step "f", 1.5-2.0 volume equivalent of a polar organic solvent (e.g., acetonitrile) is added when the remaining primary amino groups reaches 55-40% of the original primary amino. Table 2 below shows the relationship of the reagents to each other in the process just described irrespective of the scale of the process.

TABLE 2

| Step | | Amount/value | Volume of solution |
|---|---|---|---|
| a | Polyamine primary amino in solution A (moles) | W | Y |
| b | Protective chain carboxyl in solution B (moles) | 0.5-1.2 × W | Z |
| b | NHSS in solution B (moles) | 1.7-4.0 × W | Z |
| b | EDC in solution B (moles) | 1.5-3.6 × W | Z |
| b | pH of solution B | 4.0-5.5 | Z |
| b | Activation time (min) | 0-30 | |
| c & d | pH of solution C | above 6.5 | |
| c & d | Primary amino in solution C (Molar) | W/(Y + Z) = 30-55 mM | |
| e | Additional EDC added to solution C until primary amine is 45 to 60% saturated [total EDC in C] (moles) | 0.5-1.2 × W [2.0-4.8 × W] | |
| f | Acetonitrile in solution D | 1.5-2.0 × vol. of solution C | |
| g | DIPEA or other tertiary amine in solution D (moles) | 0.5-6 × W | |
| h | C18-NHS in solution E (moles) | At least 0.75 × W | Sol D volume + 3° amine + C18-NHS volume |

In another aspect of the present invention, the above aforementioned process is such wherein solution B in step "b" has 0.5-1.1×W carboxyl group; 1.7-3.7×W of NHSS; and 1.5-3.3×W of EDC; wherein in step "e", 0.5-1.1×W of EDC is added to solution C. Table 3 below shows the relationship of the reagents to each other in the process just described irrespective of the scale of the process.

TABLE 3

| Step | | Amount/value | Volume of solution |
|---|---|---|---|
| a | Primary amino in solution A (moles) | W | Y |
| b | Carboxyl in solution B (moles) | 0.5-1.1 × W | Z |
| b | NHSS in solution B (moles) | 1.7-3.7 × W | Z |
| b | EDC in solution B (moles) | 1.5-3.3 × W | Z |
| b | pH of solution B | 4.0-5.5 | Z |
| b | Activation time (min) | 0-30 | |
| c & d | pH of solution C | above 6.5 | |
| c & d | Primary amino in solution C (Molar) | W/(Y + Z) = 30-55 mM | |
| e | Additional EDC added to solution C after 3 hours [total EDC in C] (moles) | 0.5-1.1 × W [2.0-4.4 × W] | |
| f | Acetonitrile in solution D | 1.5-2.0 volume of solution C | |
| g | DIPEA or other tertiary amine in solution D (moles) | 0.5-6 × W | |
| h | C18-NHS in solution E (moles) | At least 0.75 × W | Sol D volume + 3° amine + C18-NHS volume |

In another aspect of the present invention, the above aforementioned process is such wherein solution B in step "b" has 0.5-1.0×W carboxyl group; 1.7-3.4×W of NHSS; 1.5-3.0×W of EDC; wherein activation is allowed to proceed for 5-25 min; wherein in step "e", 0.5-1.0×W additional EDC is added to solution C. Table 4 below shows the relationship of the reagents to each other in the process just described irrespective of the scale of the process.

TABLE 4

| Step | | Amount/value | Volume of solution |
|---|---|---|---|
| A | Primary amino in solution A (moles) | W | Y |
| B | Carboxyl in solution B (moles) | 0.5-1.0 × W | Z |
| B | NHSS in solution B (moles) | 1.7-3.4 × W | Z |
| B | EDC in solution B (moles) | 1.5-3.0 × W | Z |
| B | pH of solution B | 4.0-5.5 | Z |
| B | Activation time (min) | 5-25 | |
| c & d | pH of solution C | above 6.5 | |

TABLE 4-continued

| Step | | Amount/value | Volume of solution |
|---|---|---|---|
| c & d | Primary amino in solution C (Molar) | W/(Y + Z) = 30-55 mM | |
| E | Additional EDC added to solution C [total EDC in C] (moles) | 0.5-1.0 × W [2.0-4.0 × W] | |
| F | Acetonitrile in solution D | 1.5-2.0 volume of solution C | |
| G | DIPEA or other tertiary amine in solution D (moles) | 0.5-6 × W | |
| H | C18-NHS (moles) | At least 0.75 × W | Sol D volume + DIPEA + C18-NHS volume |

In another aspect of the present invention, the above aforementioned process is such wherein solution B in step "b" has 0.85-0.95×W carboxyl group; 2.6-3.2×W of NHSS; 2.5-2.9×W of EDC; wherein the pH of solution B is 4.4-5.0; wherein activation is allowed to proceed for 18-22 min; wherein in step "e", 0.85-0.95×W of EDC is added to solution C; wherein the pH of solution C is adjusted to 7-8; wherein in step "g", 1-3×W DIPEA or other tertiary amine is added to solution D. Table 5 below shows the relationship of the reagents to each other in the process just described irrespective of the scale of the process.

TABLE 5

| Step | | Amount/value | Volume of solution |
|---|---|---|---|
| a | Primary amino in solution A (moles) | W | Y |
| b | Carboxyl in solution B (moles) | 0.85-0.95 × W | Z |
| b | NHSS in solution B (moles) | 2.6-3.2 × W | Z |
| b | EDC in solution B (moles) | 2.5-2.9 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.85-0.95 × W [3.4-3.9 × W] | |
| f | Acetonitrile in solution D | 1.5-2.0 volume of solution C | |
| g | DIPEA or other tertiary amine in solution D (moles) | 1-3 × W | |
| h | C18-NHS (moles) | At least 0.75 × W | Sol D volume + DIPEA + C18-NHS volume |

In another aspect of the present invention, the above aforementioned process is such wherein solution B in step "b" has 0.9×W carboxyl group; 2.7×W of NHSS; 2.7×W of EDC; wherein the pH of solution b is 4.4-5.0; wherein activation is allowed to proceed for 18-22 min; wherein the pH of solution C is adjusted to 7-8; wherein in step "e", 0.9×W additional EDC is added to solution C. Table 6 below shows the relationship of the reagents to each other in the process just described irrespective of the scale of the process.

TABLE 6

| Step | | Amount/value | Volume of solution |
|---|---|---|---|
| a | Primary amino in solution A (moles) | W | Y |
| b | Carboxyl in solution B (moles) | 0.9 × W | Z |
| b | NHSS in solution B (moles) | 2.7 × W | Z |
| b | EDC in solution B (moles) | 2.7 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.9 × W [3.6 × W] | |

TABLE 6-continued

| Step | | Amount/value | Volume of solution |
|---|---|---|---|
| f | Acetonitrile in solution D | 1.5-2.0 volume of solution C | |
| g | DIPEA or other tertiary amine in solution D (moles) | 1-3 × W | |
| h | C18-NHS (moles) | At least 0.75 × W | Sol D volume + 3° amine + C18-NHS volume |

In another aspect of the present invention, the above aforementioned process is such wherein solution B in step "b" has 0.75-0.85×W carboxyl group, 2.3-2.8×W of NHSS, and 2.3-2.6×W of EDC; wherein the pH of solution B is 4.4-5.0; wherein activation is allowed to proceed for 18-22 min; wherein the pH of solution C is adjusted to 7-8; wherein in step "e", 0.75-0.85×W of EDC is added to solution C; wherein in step "g", 1-3×W DIPEA or other tertiary amine is added to solution D. Table 7 below shows the relationship of the reagents to each other in the process just described irrespective of the scale of the process.

TABLE 7

| Step | | Amount/value | Volume of solution |
|---|---|---|---|
| a | Primary amino in solution A (moles) | W | Y |
| b | Carboxyl in solution B (moles) | 0.75-0.85 × W | Z |
| b | NHSS in solution B (moles) | 2.3-2.8 × W | Z |
| b | EDC in solution B (moles) | 2.3-2.6 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.75-0.85 × W [3.1-3.5 × W] | |
| f | Acetonitrile in solution D | 1.5-2.0 volume of solution C | |
| g | DIPEA or other tertiary amine in solution D (moles) | 1-3 × W | |
| h | C18-NHS (moles) | At least 0.75 × W | Sol D volume + 3° amine + C18-NHS volume |

In another aspect of the present invention, the above aforementioned process is such wherein solution B in step "b" has 0.8×W carboxyl group; 2.4×W of NHSS; 2.4×W of EDC; wherein the pH of solution B is 4.4-5.0; wherein activation is allowed to proceed for 18-22 min; wherein the pH of solution C is adjusted to 7-8; wherein in step "e", 0.8×W additional EDC is added to solution C; wherein in step "e" at least 0.75×W C18-NHS is added. Table 8 below shows the relationship of the reagents to each other in the process just described irrespective of the scale of the process.

TABLE 8

| Step | | Amount/value | Volume of solution |
|---|---|---|---|
| a | Primary amino in solution A (moles) | W | Y |
| b | Carboxyl in solution B (moles) | 0.8 × W | Z |
| b | NHSS in solution B (moles) | 2.4 × W | Z |
| b | EDC in solution B (moles) | 2.4 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.8 × W [3.2 × W] | |
| f | Acetonitrile in solution D | 1.5-2.0 volume of solution C | |

TABLE 8-continued

| Step | | Amount/value | Volume of solution |
|---|---|---|---|
| g | DIPEA or other tertiary amine in solution D (moles) | 1-3 × W | |
| h | C18-NHS (moles) | At least 0.75 × W | Sol D volume + 3° amine + C18-NHS volume |

In another aspect of the present invention, the above aforementioned process is such wherein solution B in step "b" has 0.65-0.75×W carboxyl group, 2.0-2.5×W of NHSS, 2.0-2.3×W of EDC; wherein the pH of solution B is 4.4-5.0; wherein activation is allowed to proceed for 18-22 min; wherein the pH of solution C is adjusted to 7-8; wherein in step "e", 0.65-0.75×W of EDC is added to solution C; wherein in step "g", 1-3×W DIPEA or other tertiary amine is added to solution D. Table 9 below shows the relationship of the reagents to each other in the process just described irrespective of the scale of the process.

TABLE 9

| Step | | Amount/value | Volume of solution |
|---|---|---|---|
| a | Primary amino in solution A (moles) | W | Y |
| b | Carboxyl in solution B (moles) | 0.65-0.75 × W | Z |
| b | NHSS in solution B (moles) | 2.0-2.5 × W | Z |
| b | EDC in solution B (moles) | 2.0-2.3 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.65-0.75 × W [2.7-3.1 × W] | |
| f | Acetonitrile in solution D | 1.5-2.0 volume of solution C | |
| g | DIPEA or other tertiary amine in solution D (moles) | 1-3 × W | |
| h | C18-NHS (moles) | At least 0.75 × W | Sol D volume + 3° amine + C18-NHS volume |

In another aspect of the present invention, the above aforementioned process is such wherein solution B in step "b" has 0.7×W carboxyl group; 2.1×W of NHSS; 2.1×W of EDC; wherein the pH of solution B is 4.4-5.0; wherein activation is allowed to proceed for 18-22 min; wherein the pH of solution C is adjusted to 7-8; wherein in step "e", 0.7×W additional EDC is added to solution C; wherein in step "g", 1-3×W DIPEA or other tertiary amine is added to solution D. Table 10 below shows the relationship of the reagents to each other in the process just described irrespective of the scale of the process.

TABLE 10

| Step | | Amount/value | Volume of solution |
|---|---|---|---|
| a | Primary amino in solution A (moles) | W | Y |
| b | Carboxyl in solution B (moles) | 0.7 × W | Z |
| b | NHSS in solution B (moles) | 2.1 × W | Z |
| b | EDC in solution B (moles) | 2.1 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.7 × W [2.8 × W] | |
| f | Acetonitrile in solution D | 1.5-2.0 volume of solution C | |
| g | DIPEA or other Tertiary amine in solution D (moles) | 1-3 × W | |

TABLE 10-continued

| Step | | Amount/value | Volume of solution |
|---|---|---|---|
| h | C18-NHS (moles) | At least 0.75 × W | Sol D volume + 3° amine + C18-NHS volume |

In another aspect of the present invention, the above aforementioned process is such wherein solution B in step "b" has 0.55-0.65×W carboxyl group, 1.7-2.2×W of NHSS, 1.7-2.0×W of EDC; wherein the pH of solution B is 4.4-5.0; wherein activation is allowed to proceed for 18-22 min; wherein the pH of solution C is adjusted to 7-8; wherein in step e, 0.55-0.65×W of EDC is added to solution C; wherein in step "g", 1-3×W DIPEA or other tertiary amine is added to solution D. Table 11 below shows the relationship of the reagents to each other in the process just described irrespective of the scale of the process.

TABLE 11

| Step | | Amount/value | Volume of solution |
|---|---|---|---|
| a | Primary amino in solution A (moles) | W | Y |
| b | Carboxyl in solution B (moles) | 0.55-0.65 × W | Z |
| b | NHSS in solution B (moles) | 1.7-2.2 × W | Z |
| b | EDC in solution B (moles) | 1.7-2.0 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.55-0.65 × W [2.3-2.7 × W] | |
| f | Acetonitrile in solution D | 1.5-2.0 volume of solution C | |
| g | DIPEA or other tertiary amine in solution D (moles) | 1-3 × W | |
| h | C18-NHS (moles) | At least 0.75 × W | Sol D volume + 3° amine + C18-NHS volume |

In another aspect of the present invention, the above aforementioned process is such wherein solution B in step "b" has 0.6×W carboxyl group; 1.8×W of NHSS; 1.8×W of EDC; wherein the pH of solution B is 4.4-5.0; wherein activation is allowed to proceed for 18-22 min; wherein the pH of solution C is adjusted to 7-8; wherein in step "e", 0.6×W additional EDC is added to solution C; wherein in step "e" at least 0.75×W C18-NHS is added. Table 12 below shows the relationship of the reagents in the process just described to each other irrespective of the scale of the process.

TABLE 12

| Step | | Amount/value | Volume of solution |
|---|---|---|---|
| a | Primary amino in solution A (moles) | W | Y |
| b | Carboxyl in solution B (moles) | 0.6 × W | Z |
| b | NHSS in solution B (moles) | 1.8 × W | Z |
| b | EDC in solution B (moles) | 1.8 × W | Z |
| b | pH of solution B | 4.4-5.0 | Z |
| b | Activation time (min) | 18-22 | |
| c & d | pH of solution C | 7-8 | |
| c & d | Primary amino in solution C (Molar) | W/(Y + Z) = 30-55 mM | |
| e | Additional EDC added to solution C [total EDC in C] (moles) | 0.6 × W [2.4 × W] | |
| f | Acetonitrile in solution D | 1.5-2.0 volume of solution C | |
| g | DIPEA or other tertiary amine in solution D (moles) | 1-3 × W | |

TABLE 12-continued

| Step | | Amount/value | Volume of solution |
|---|---|---|---|
| h | C18-NHS (moles) | At least 0.75 × W | Sol D volume + 3° amine + C18-NHS volume |

As described herein, the present invention includes alternatives within steps (f), (g), and (h) of the above aforementioned processes, wherein: (f) comprises freezing and lyophilizing solution C when the remaining primary amino groups is 55-40% of the original primary amino and reconstituting the lyophilized material with water-immiscible organic solvent such as dichloromethane or a mixture of water-miscible and water-immiscible organic solvents to obtain solution D; (g) comprises adding 0.5-6×W DIPEA or other tertiary amine to solution D; (h) comprises adding at least 0.75×W equivalent of C18-NHS directly or in appropriate solvent such as dichloromethane to obtain solution E and stirring the solution at room temperature for at least 2 hours until the remaining primary amino groups is less than 5% of the original primary amino to obtain the crude final product.

The above aforementioned processes, wherein the final product in solution E is in organic solvent, may further comprise step (i) exchanging the organic solvent in the crude product into water and washing the product by ultrafiltration using at least 10 exchanges of ethanol and water.

As described herein, the present invention includes further alternatives within steps (f), (g), and (h) of above aforementioned processes, wherein: (f) comprises adding a strong nucleophile (at least 1×W equivalent of the original primary amino) such as hydroxyl amine to solution C and purifying the product by ultrafiltration as described below followed by lyophilization and dissolving in a polar organic solvent (e.g., acetonitrile) to obtain solution D; (g) comprises adding 0.5-6×W DIPEA or other tertiary amine to solution D; (h) comprises adding at least 0.75×W equivalent of C18-NHS to obtain solution E and stirring the solution at room temperature for at least 2 hours or until the remaining primary amino groups is less than 5% of the original primary amino to obtain the crude final product.

The above aforementioned processes, wherein the final product in solution E is in a mixture of water and water-miscible organic solvent, may further comprise step (i) extracting the water-miscible organic solvent and excess fatty acids from the crude final product in solution E using a polar organic solvent (e.g., ethyl acetate) and discarding the polar organic solvent (e.g., ethyl acetate) layer and repeating the extraction of the water layer at least once followed by washing the product by ultrafiltration using at least 10 exchanges of ethanol and water.

Definitions

For convenience, before further description of the present disclosure, certain terms employed in the specification, examples, and appended claims are collected here. These definitions should be read in light of the remainder of the disclosure and understood as by a person of ordinary skill in the art. Unless defined otherwise, all technical and scientific terms used herein have the same meaning as commonly understood by a person of ordinary skill in the art. Unless otherwise indicated the general mathematical rule of rounding off numbers applies to all the numbers in the present specification with the exception of molecular weight of a non-poly-disperse molecule such as for example $H_2O$, NHSS, EDC etc. Polymers are poly-disperse molecules. Whenever a number is given the last digit of the number is understood to be the limit of certainty and is a result of rounding off the range of numbers to the nearest last digit of a given number. For example the "5 kDa polymer" means a range between 4.5 kDa to 5.5 kDa since rounding of 4.51-5.49 kDa to the nearest thousand is 5 kDa. Another example is 2.1 mmol is a range between of 2.05 to 2.15 mmol. Another example is 5.0 kDa polymer is a range between 4.95 to 5.05 kDa.

The articles "a" and "an" are used to refer to one or to more than one (i.e., to at least one) of the grammatical object of the article. By way of example, "a protective chain" means one protective chain or more than one protective chain.

The term "ANP" is Atrial Natriuretic Peptide (sequence based on convention known in the art: SEQ ID NO: 1-SLRRSSCFGGRMDRIGAQSGLGCNSFRY with intrapeptide disulfide bond). This peptide was used for the purpose of the present specification to distinguish the differences between graft co-polymers produced by various processes.

The term "BNP" is a B type Natriuretic Peptide (sequence based on convention known in the art: SEQ ID NO: 2-SPKMVQGSGCFGR KMDRISSSSG LGCKVLRRH with intrapeptide disulfide bond). This peptide was used for the purpose of the present specification to distinguish the differences between graft co-polymers produced by various processes.

The terms "C12-NHS", "C13-NHS", "C14-NHS", "C15-NHS", "C16-NHS", "C17-NHS", "C18-NHS", "C19-NHS", "C20-NHS", "C21-NHS", etc. refer to fatty acids with aliphatic tails of 12 to 21 carbons in which the carboxyl group is esterified with NHS, see "fatty acids" below. Unless otherwise stated, C12 refers to lauric acid, C14 refers to myristic acid, C16 refers to palmitic acid, C18 refers to stearic acid, and C20 refers to arachidic acid.

The term "derivative" or "analog" as used herein refers to a compound whose core structure is the same as, or closely resembles that of, a parent compound but which has a chemical or physical modification such as different or additional groups. The term also includes a peptide with at least 80% sequence identity (i.e. amino acid substitution is less than 20%) with the parent peptide. The term also includes a peptide with additional groups attached to it compared to the parent peptide, such as fatty acids and/or additional amino acids. The term also includes a polymer with additional group(s) attached to it, such as, in the case of a protective group, an alkoxy group, compared to the parent polymer. The term also includes methoxylated or ethoxylated protective chains with additional methoxy or ethoxy-group(s) attached to it, compared to the parent protective chains.

The term "DIPEA" refers to N,N-Diisopropylethylamine, or Hünig's base, or DIEA, an organic compound and an amine. It is used in organic chemistry as a base. Because the nitrogen atom is shielded by the two isopropyl groups and an ethyl group, only a proton is small enough to easily fit. Like 2,2,6,6-tetramethylpiperidine, this compound is a good base but a poor nucleophile, which makes it a useful organic reagent.

The term "EDC" refers to 1-Ethyl-3-(3-dimethylaminopropyl)carbodiimide HCl which can also be referred to as EDAC or EDCI and has a Molecular Weight: 191.70 Da. This carbodiimide reagent contains a functional group consisting of the formula N=C=N which is necessary for activation of carboxyl groups; this group is important for activating carboxyl groups on the protective chain and the fatty acids. During the process of the coupling reactions, the activated carboxyl group O-acylisourea-intermediate can be stabilized by forming N-hydroxysuccinimide ester with either N-hydroxysuccinimide or N-hydroxysulfosuccinimide.

The term "fatty acid" is a carboxylic acid with a long aliphatic tail or chain), which is either saturated or unsaturated. Most naturally occurring fatty acids have a tail of an even number of carbon atoms, from 4 to 28. When they are not attached to other molecules, they are known as "free" fatty acids. Fatty acids that have carbon-carbon double bonds are known as unsaturated and those without double bonds are known as saturated. Fatty acid chains differ by length, often categorized as short to very long. Short-chain fatty acids are fatty acids with aliphatic tails of fewer than six carbons (i.e. butyric acid). Medium-chain fatty acids are fatty acids with aliphatic tails of 6 to 12 carbons (also called C6-C12 fatty acids, where the number refers to the number of carbons). Long-chain fatty acids are fatty acids with aliphatic tails 13 to 21 carbons (also called C13-C21 fatty acids). Very long chain fatty acids are fatty acids with aliphatic tails longer than 22 carbons (also called ≥C22 fatty acids). For the purpose of the present specification, the term "fatty acid" covers all of the above and each of the species of fatty acid may have more than one common name. Examples of saturated fatty acids includes caprylic acid ($CH_3(CH_2)_6COOH$), capric acid ($CH_3(CH_2)_8COOH$), lauric acid ($CH_3(CH_2)_{10}COOH$), myristic acid ($CH_3(CH_2)_{12}COOH$), palmitic acid ($CH_3(CH_2)_{14}COOH$), stearic acid ($CH_3(CH_2)_{16}COOH$), arachidic acid ($CH_3(CH_2)_{18}COOH$), behenic acid ($CH_3(CH_2)_{20}COOH$), lignoceric acid ($CH_3(CH_2)_{22}COOH$), cerotic acid ($CH_3(CH_2)_{24}COOH$). Examples of unsaturated fatty acids includes myristoleic acid ($CH_3(CH_2)_3CH=CH(CH_2)_7COOH$), palmitoleic acid ($CH_3(CH_2)_5CH=CH(CH_2)_7COOH$), sapienic acid ($CH_3(CH_2)_8CH=CH(CH_2)_4COOH$), oleic acid ($CH_3(CH_2)_7CH=CH(CH_2)_7COOH$), elaidic acid ($CH_3(CH_2)_7CH=CH(CH_2)_7COOH$), vaccenic acid ($CH_3(CH_2)_5CH=CH(CH_2)_9COOH$), linoleic acid ($CH_3(CH_2)_4CH=CHCH_2CH=CH(CH_2)_7COOH$), linoelaidic acid ($CH_3(CH_2)_4CH=CHCH_2CH=CH(CH_2)_7COOH$), α-linolenic acid ($CH_3CH_2CH=CHCH_2CH=CHCH_2CH=CH(CH_2)_7COOH$), arachidonic acid ($CH_3(CH_2)_4CH=CHCH_2CH=CHCH_2CH=CHCH_2CH=CH(CH_2)_3COOH$), eicosapentaenoic acid ($CH_3CH_2CH=CHCH_2CH=CHCH_2CH=CHCH_2CH=CHCH_2CH=CH(CH_2)_3COOH$), erucic acid ($CH_3(CH_2)_7CH=CH(CH_2)_{11}COOH$), docosahexaenoic acid ($CH_3CH_2CH=CHCH_2CH=CHCH_2CH=CHCH_2CH=CHCH_2CH=CHCH_2CH=CH(CH_2)_2COOH$).

The term "fatty acid-NHS" refers to the fatty acid in which the carboxyl group is esterified with NHS. The term "long chain fatty acid-NHS" refers to the long-chain fatty acids or fatty acids with aliphatic tails 13 to 21 carbons (also called C13-C21 fatty acids, where the number refers to the number of carbons) in which the carboxyl group is esterified with NHS. Similar naming applies to "short long chain fatty acid-NHS" where the fatty acids have aliphatic tails of 6 to 12 carbons. Again similar naming applies to "very long chain fatty acid-NHS" where the fatty acids have aliphatic tails of 22 carbons and greater.

The term "Fatylation" refers to a step or a chemical process of adding a fatty acid to a polyamine backbone.

The term "GLP-1" refers to glucagon like peptide-1 (sequence SEQ ID NO: 3-HAEGTFTSDV SSYLEGQAAK EFIAWLVKGR G). This peptide was used for the purpose of the present specification to distinguish the differences between graft co-polymers produced by various processes.

The term "HEPES" refers to 4-(2-hydroxyethyl)-1-piperazineethanesulfonic acid and is a zwitterionic organic chemical buffering agent with high buffering capacity between pH 6.5 and 8.5.

The term "linear polyamine backbone" refers to a straight chain non-proteinaceous homo- or hetero-polymer with repeating primary amino groups and may be of natural or synthetic origin. Non-proteinaceous meaning that it is not a protein made by a living organism to have a three dimensional conformation associated with cellular activity. The "linear polyamine backbone" is used interchangeably with "linear polymeric backbone" and is a component of solution A in this specification. The preferred straight "linear polyamine backbone" is polylysine and is also referred to as PL in this specification. The "linear polyamine backbone" can be other polyamino acids which may have D- or L-chirality, or both, in which the side group of the amino acid (known as the R-group) contains a primary amine. Often, the polymeric backbone may have an average number molecular weight (Mn) of 5-95 kDa or a degree of polymerization (DPn) of 22-450 based on light scattering or nuclear magnetic resonance analysis. The preferred polymeric backbone has a Mn of 7-32 kDa or a DPn of 35-150 based on light scattering or nuclear magnetic resonance analysis. The most preferred polymeric backbone has a Mn of 7-18 kDa or a DPn of 35-85 based on light scattering or nuclear magnetic resonance analysis. By viscosity measurement the DPns given above can be twice as high for the same material depending on what standard is used. Other polymeric backbones with repeating primary amino groups may also be used such carbohydrate polymers or other synthetic polymers. The polymeric backbone provides the multiple primary amino groups to which the protective chains and fatty acids can be attached.

The term "% loading" is defined as a binding characteristic where peptide is mixed with the semi-random graft co-polymer product at a defined weight-to-weight ratio of peptide:co-polymer in a physiological or near physiological buffer, for example 10% loading consists of 1 part peptide and 10 parts co-polymer, by weight. The percentage of free peptide at particular loadings is used to distinguish differences between graft co-polymers produced by various processes.

The term "protective side chain" as used herein refers to a hydrophilic polymer molecule that has the ability to extensively bind or imbibe water along the chain and is a component of solution B. Bind or imbibe is different from absorb which is refers to uptake into the spaces or channels of a large molecular structure such as sponge, a resin, or gel. Because of this extensive binding with water molecules, the protective chain has high water solubility and it also increases the water solubility of other polymers to which it is linked. The protective side chain does not have a significant amount of charge and is generally non-immunogenic. This also means that the protective chain provides a hydrophilic property to the composition that would otherwise be less water soluble. The term "protective chain" and "protective side chain" are used in this specification interchangeably. The protective chains of the present composition typically include polyoxyethylene glycol, also referred to as polyethylene glycol, which may or may not be alkoxylated (such as methoxy or ethoxy) at one end but terminates with a carboxyl moiety at the other end. The protective chains may also or alternatively be polypropylene glycol or polyethylene-polypropylene glycol co-polymer, which may or may not be alkoxylated (such as methoxy or ethoxy) at one end but all terminate with a carboxyl moiety. The preferred protective chain is a linear methoxylated polyethyleneglycol (MPEG or methoxyPEG) with carboxyl terminus and which ranges in size from 2 to 20 kDa based on gel permeation chromatography standardized with the same or similar materials. The more preferred size is 4-12 kDa and the most preferred size is 4-6 kDa. The protective chains of the present composition also include uncharged polysaccharides and their derivatives such as ethoxylated or methoxylated polysaccharides. In this context, uncharged means that the main body of the chain does not have positive or negative charge.

The term "MPEG-CM" refers to methoxypolyethyleneglycol-carboxyl and is a linear PEG with methoxy group at one end and a carboxyl group at the other end. This is a non-pre-activated form of PEG.

The term "MPEG-SCM" refers to methoxypolyethyleneglycol succinimidyl succinate and is an NHS pre-activated form of linear PEG with a methoxy group at one end and an NHS linked carbonyl group at the other end.

The term "NHS" refers to N-hydroxysuccinimide and has a molecular weight: 115.10 Da.

The term "NHSS" refers to N-hydroxysulfosuccinimide and has a molecular weight: 217.14 Da.

The term "non-water miscible organic solvent" means that the organic solvent mixes with water or dissolves in water at less than 50% wt/wt. For example: dichloroethane, benzene, butyl acetate, carbon tetrachloride, chlorobenzene, chloroform, Cyclohexane, diethyl ether, di-isopropylether, dichloromethane, ethyl acetate, ethylbenzene, methyl ethyl ketone, methyl butyl ether, n-butanol, pentane, n-hexane, heptane, toluene, tetrachloroethylene, and xylene.

The term "PEGylation" refers to a step or a chemical process of adding PEG or its derivative to a polyamine backbone.

The term "primary amines" refers to a nitrogen bonded to one alkyl or aromatic ring and 2 hydrogen atoms. In other words, it is a nitrogen where one of the three hydrogen sites is replaced by an organic substituent. Important primary amines for the purpose of this specification are the repeating primary amine moieties along the linear polyamine backbone. In the case of polylysine, it is the epsilon primary amino group of lysine along the polylysine polymer.

The term "Sol" refers to solution and for the purpose of the present specification refers to various liquid solutions A through E designated Sol A to Sol E.

The term "strong nucleophiles" refers to reagents that get easily deprotonated to give anions with a full negative charge, are easily recognizable by the presence of sodium, lithium, or potassium counterions, and participate in SN2-type substitutions. Examples of strong nucleophile include $NH_2OH$, $NaOCH_3$ (any $NaOR$), $LiCH_3$ (any $LiR$), $NaOH$ or $KOH$, $NaCN$ or $KCN$, $NaCCR$ (acetylide anion), $NaNH_2$, $NaNHR$, $NaNR_2$, $NaI$, $LiBr$, $KI$, and $NaN_3$. A strong nucleophile can be used to stop the reaction in Sol C of the present disclosure to interrupt the process at a specific stage for purification and/or evaluation of intermediate.

The term "TEA" refers to triethylamine is the chemical compound with the formula $N(CH_2CH_3)_3$, commonly abbreviated $Et_3N$. It is also abbreviated TEA, yet this abbreviation must be used carefully to avoid confusion with triethanolamine or tetraethylammonium, for which TEA is also a common abbreviation. Like diisopropylethylamine (Hünig's base), triethylamine is commonly encountered in organic synthesis.

The term "TEOA" refers to triethanolamine or 2,2',2"-trihydroxy-triethylamine or tris(2-hydroxyethyl) amine, also abbreviated as TEA, is a viscous organic compound that is both a tertiary amine and a triol.

The term "tertiary amines" refers to a nitrogen where the three hydrogen sites are replaced by three organic substituents. Examples include trimethylamine (TEA), N,N-diisopropylethylamine (DIPEA), and triphenylamine.

The term "TNBS" refers to Trinitrobenzenesulfonic acid ($C_6H_3N_3O_9S$) which is a nitro-aryl oxidizing acid. For the purpose of this specification, an assay utilizing TNBS is used to measure primary amine according to Spadaro, A. C., et al., (A convenient manual trinitrobenzenesulfonic acid method for monitoring amino acids and peptides in chromatographic column effluents. (Anal. Biochem., 1979, 96(2): p. 317-21) in solutions A, C, and E. The use of the TNBS assay for primary amine is to determine the primary amino group saturation of solution C so the reaction can go to the next step.

The term "water-miscible organic solvent" means that the organic solvent mixes with water or dissolves in water at 50% wt/wt or greater, for example acetic acid, acetonitrile, acetone, dimethyl formamide, dimethyl sulfoxide, dioxane, ethanol, isopropanol, n-propanol, methanol, and tetrahydrofuran.

The term "W" refers to the total number of moles of primary amino group present in the starting polyamine backbone in solution A or original amino groups in solution A of the process. The use of the term allows for the process to be increased to industrial scale. For the purpose of clarity, critical reagents in this specification are expressed as fractions or multiples of "W".

The term "×W" refers to multiples of W and is usually preceded by a number that will be multiplied by W to give a specific value or amount of critical reagent needed. For example if W is equal to 2.6 mmol and a protective chain has a carboxyl equivalent of 0.9×W, then that amount will be 0.9'2.6 mmol, or 2.34 mmol.

As used herein, a $C_1$ to $C_6$ alkyl group is a linear or branched alkyl group containing from 1 to 6 carbon atoms. Typically a $C_1$ to $C_6$ alkyl group is a $C_1$ to $C_4$ alkyl group, which is a linear or branched alkyl group containing from 1 to 4 carbon atoms. A $C_1$ to $C_4$ alkyl group is often a $C_1$ to $C_3$ alkyl group. Examples of $C_1$ to $C_6$ alkyl groups include methyl, ethyl, n-propyl, iso-propyl, n-butyl, sec-butyl, tert-butyl, pentyl and hexyl. A $C_1$ to $C_3$ alkyl group is typically a $C_1$ to $C_2$ alkyl group. A $C_1$ to $C_2$ alkyl group is methyl or ethyl, typically methyl. For the avoidance of doubt, where two alkyl groups are present, the alkyl groups may be the same or different.

As used herein, a $C_2$ to $C_6$ alkenyl group is a linear or branched alkenyl group containing from 2 to 6 carbon atoms and having one or more, e.g. one or two, double bonds. Typically a $C_2$ to $C_6$ alkenyl group is a $C_2$ to $C_4$ alkenyl group, e.g. a $C_2$ to $C_3$ alkenyl group. Examples of $C_2$ to $C_6$ alkenyl groups include ethenyl, propenyl, butenyl, pentenyl and hexenyl. For the avoidance of doubt, where two alkenyl groups are present, the alkenyl groups may be the same or different.

By way of example, in the methods of the invention, the linear polyamine backbone is often polylysine with degree of polymerization of 22-450, more often 35-150, still more often 35-85 based on light scattering or nuclear magnetic resonance analysis; the protective chain is often methoxy PEG chain with single carboxyl terminus having 2-20 kDa, more often 4-12 kDa, still more often 4-6 kDa number average molecular weight or Mn based on gel permeation chromatography; and the long chain fatty acid-NHS is often C18-NHS.

The following Examples illustrate the invention. They do not however, limit the invention in any way. In this regard, it is important to understand that the particular assays used in the Examples section are designed only to provide an indication of binding capacity of the peptide. There are many assays available to determine such capacity, and a negative result in any one particular assay is therefore not determinative.

EXAMPLES

The Examples herein describe processes of synthesis that give a semi-random graft co-polymer product that is an efficient binder of a model peptide called Atrial Natriuretic Peptide (ANP; sequence based on convention known in the art: SEQ ID NO: 1 SLRRSSCFGGRMDRI-GAQSGLGCNSFRY with intrapeptide disulfide bond). The term "efficient binder" is defined as a binding characteristic such that when peptide is mixed with the semi-random graft co-polymer product at a weight ratio of 1:10 (Peptide:Co-polymer, wt:wt) in a physiological or near physiological buffer the amount of free peptide (evaluated as described below) will be less than 12%. Such a binder does not exist prior to the disclosure of the present disclosure.

It should be noted that, for any given co-polymer binder, as the weight ratio of peptide to co-polymer increases the amount of free peptide increases and, conversely, as the weight ratio of peptide to co-polymer decreases the amount of free peptide decreases. This is because the co-polymer, the subject of the present disclosure, is a reversible binder that has properties that include capacity. If the capacity is saturated by peptide due to higher loading, any additional peptide will not bind. Because of the complexity of the structure of the groups of co-polymer, the subject of the present disclosure, the only way to distinguish differences in composition is by comparing their measurable properties.

General
Reagents

Unless otherwise indicated, reagents were used without further purification. In addition, the reagents that were used are commercially available and their syntheses are well known in the art.

Poly-L-lysine hydrobromide (PL), DPn by NMR 55, Mm by NMR 11,500, PDI by GPC 1.04, was from Alamanda Polymers (Huntsville, Ala.); methoxypolyethyleneglycol-carboxyl (MPEG-CM), MW 5 kDa was from Laysan Bio Inc (Arab, Ala.); N-hydroxysuccinimidesulfate (NHSS), MW 217 Da was from ChemPep (Wellington, Fla.); methoxy-polyethyleneglycol succinimidyl succinate (MPEG-SCM), MW 5 kDa was from JenKem Technology USA (Plano, Tex.); and 1-Ethyl-3-(3-dimethylaminopropyl)carbodiimide (EDC), MW 192 Da was from Pierce (Rockford, Ill.). Stearic acid (C18), MW 284 Da was from Alfa Aesar (Ward Hill Mass.); N-Hydroxysuccinimide (NHS), MW 115 Da was from Acros Organics (Pittsburgh, Pa.); and N,N'-dicy-clohexylcarbodiimide (DCC), MW 206 Da was from Acros Organics (Pittsburgh, Pa.).

General Techniques

The method modified from Lapidot et al. [Lapidot, Y., Rappoport, S. and Wolman, Y. (1967) J. Lipid Res., 8, 142] was used to prepare stearic acid N-hydroxysuccinimide ester (C18-NHS), MW 382 Da. Stearic acid (MW 284 Da, 17 gm, 60 mmol) in 230 mL ethyl acetate was activated with NHS (MW 115 Da, 6.9 g, 60 mmol) and DCC (MW 206 Da, 9.6 mL, 12.4 g, 60 mmol) and incubated overnight. The urea precipitate was removed by filtration. The filtrate was then dried and recrystallized using ethanol. The product C18-NHS was collected by filtration, dried under vacuum, and stored frozen desiccated.

Buffers were prepared in deionized distilled water. The adjustment of reaction pH was performed using a pH meter.

The degree of PL modification by PEG and C18 was measured by assessing the consumption of free primary amino groups using a TNBS assay (Sparado et al. (1979) Anal. Biochem. 96, 317). Visible light absorbance of samples was measured using a microplate reader.

The product was washed by ultrafiltration through 100 kDa or 50 kDa cut-off membrane. Ultrafiltration was performed using membrane cartridges (UFP-100-E or UFP-50-E, GE-Amersham Biosciences Corp, Westborough, Mass.) mounted on a QuixStand system (GE-Amersham Biosciences Corp, Westborough, Mass.). Typical washing conditions use 10 volume-equivalents (relative to solution volume being washed) of 90% alcohol, 10-15 volumes of 80% alcohol and 10 volumes of water. The product was then filter-sterilized and lyophilized.

The hydrodynamic diameter of graft co-polymers was assessed by Gel permeation chromatography using TosohG4000WXL HPLC column calibrated using globular protein standards. Binding to peptide of the graft co-polymer products of various processes was evaluated by 2-hour incubation of the co-polymer with the corresponding peptide in phosphate buffered saline at pH 7.35 or 100 mM HEPES buffer pH 7.35 followed by filtration through a 100 kDa molecular weight cut-off membrane filter (regenerated cellulose filter, YM-100, from Millipore, Bedford, Mass.) by centrifugation. No difference in a peptide binding to a graft co-polymer product was observed between these two buffers.

The filtrate containing free (unbound) peptide was quantified by reverse phase HPLC (Synergi 2.5 um Max, 0.4×2 cm) monitored at 220 nm ran at a flow rate of 1.5 mL/min using a gradient of 0% B for 1 min and 25-50% B for 1-5 min, where A is 5% acetonitrile with 0.1% TFA and B is 100% acetonitrile with 0.1% TFA. The filtrate from control tubes containing peptide without the co-polymer was taken as the total amount of peptide available for binding. The amount of bound peptide can be calculated by subtracting the concentration of free peptide that passed through the filter from the corresponding control that received the same concentration of peptide but without the graft co-polymer. Binding was tested at various ratios such that 2, 5, and 10% loading represent 1:50, 1:20, and 1:10 peptide weight to co-polymer weight ratio.

Methods

Unless otherwise indicated, the synthesis of graft co-polymers was performed by preparing a series of solutions (Sol A, Sol B, Sol C, Sol D and Sol E) and combining them or by adding reagents to them during the PEGylation and Fatylation steps of the chemical process. Sol A contained PL dissolved in buffer (250 or 50 mM HEPES; or 100 mM TEOA) and Sol B contained mPEG-CM activated with NHSS and EDC in MES buffer (10 mM, pH 4.7) at room temperature. Sol C is the reaction solution where PEGylation of PL occurs and was prepared at room temperature by combining Sol A and Sol B, or by adding reagents (NHSS, EDC or PEG-SCM) directly to Sol A, thus having zero minute pre-activation and no Sol B. No solution B is different from having solution B with 0 min pre-activation. When primary amino groups, as measured by TNBS, were found to be 41-62% Sol D was prepared by adding organic solvent (acetonitrile, acetone, or dichloromethane) to solution C and heating to 55-60° C. Sol E is the reaction solution where Fatylation occurs and was prepared adding C18-NHS, and DIPEA to Sol D. Sol E was allowed to cool to room temperature and allowed to stir from two hours to overnight. A volume of water approximately equal to the volume of Sol E was added to Sol E and the solution extracted 2-3 times with 2 volumes of a polar organic solvent (e.g., ethyl acetate). The aqueous phase containing product was then diluted with distilled deionized water and washed by ultrafiltration described above. In some cases the chemical process does not require Sol B as in the case where PEG-SCM, EDC or NHSS are added to Sol A to produce Sol C. In all cases, equivalents of reagents are reported relative to the starting primary amino content of PL.

Example 1

Samples 1-A, 1-B, and 1-C

Synthesis of graft co-polymer 1-A, 1-B, and 1-C (5 kDa MPEG-CM; 20 kDa PL; 59, 53, and 54% saturation of amino groups with PEG and remaining primary amino groups modified with stearic acid) using MPEG-CM for the PEGylation reaction. The syntheses were performed as described in the General section unless specified otherwise. Activation of Sol B was allowed to proceed for 20 minutes. After 2 and 3 hrs. additional EDC was added to Sol C (total EDC reported in ratio tables for individual lots). The following tables below provide the properties of the products and the ratios of each of the reagents used during the synthesis.

TABLE 13

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 1-A | 59 | 18.8 | 1.2 | 35* |
| 1-B | 53 | 19.9 | 1.0 | 32* |
| 1-C | 54 | 20.5 | 1.1 | 29* |

*The corresponding process failed to provide products with the desired property.

The moderate binding of the synthesized graft co-polymers was not within the range of acceptable quantities for free ANP of 13% or less at 10% peptide loading. Thus, the ratio of reagents used for this process provided product that was inferior compared to the product produced by the process in the present disclosure.

TABLE 14

Ratios for Sample 1-A in Example 1

| Step | | Amount/value | Volume of solution |
|---|---|---|---|
| a | Amino in solution A (moles) | W = 0.620 mmol | Y = 4 mL |
| b | Carboxyl in solution B (moles) | 0.771W | Z = 8 mL |
| b | NHSS in solution B (moles) | 0.871W | Z = 8 mL |
| b | EDC in solution B (moles) | 1.58W | Z = 8 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 51.7 mM | |
| e | Additional EDC added to solution C [total EDC in C] (moles) | 1.87 × W [3.45 × W] | |
| f | Acetonitrile in Sol D | 20.5 mL | |
| g | DIPEA in solution D (moles) | 2.47 × W | |
| h | C18-NHS in solution E (moles) | 1.12 × W | Sol D volume + C18-NHS volume = 39.7 mL |

TABLE 15

Ratios for Sample 1-B in Example 1

| Step | | Amount/value | Volume of solution |
|---|---|---|---|
| a | Amino in solution A (moles) | W = 0.578 mmol | Y = 4 mL |
| b | Carboxyl in solution B (moles) | 0.827 × W | Z = 8 mL |
| b | NHSS in solution B (moles) | 0.934 × W | Z = 8 mL |
| b | EDC in solution B (moles) | 1.41 × W | Z = 8 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 48.2 mM | |
| e | Additional EDC added to solution C [total EDC in C] (moles) | 2.42 × W [3.83 × W] | |
| f | Acetonitrile in Sol D | 20.5 mL | |
| g | DIPEA in solution D (moles) | 2.65 × W | |

TABLE 15-continued

Ratios for Sample 1-B in Example 1

| Step | Amount/value | Volume of solution |
|---|---|---|
| h | C18-NHS in solution E (moles) At least 1.21 × W | Sol D volume + C18-NHS volume = 39.7 mL |

TABLE 16

Ratios for Sample 1-C in Example 1

| Step | | Amount/value | Volume of solution |
|---|---|---|---|
| a | Amino in solution A (moles) | W = 0.571 mmol | Y = 4 mL |
| b | Carboxyl in solution B (moles) | 0.837 × W | Z = 8 mL |
| b | NHSS in solution B (moles) | 0.946 × W | Z = 8 mL |
| b | EDC in solution B (moles) | 1.34 × W | Z = 8 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 47.5 mM | |
| e | Additional EDC added to solution C [total EDC in C] (moles) | 2.39 × W [3.73 × W] | |
| f | Acetonitrile in Sol D | 20.5 mL | |
| g | DIPEA in solution D (moles) | 2.68 × W | |
| h | C18-NHS in solution E (moles) | 1.22 × W | Sol D volume + C18-NHS volume = 39.7 mL |

Example 2

Samples 2-A, 2-B, and 2-C

Synthesis of graft co-polymer 2-A, 2-B, and 2-C (5 KDa MPEG-CM; 20 kDa PL; 45, 44, and 44% saturation of primary amino groups with PEG and remaining primary amino groups modified with stearic acid) using MPEG-CM for the PEGylation reaction. The syntheses were performed as described in the General section unless specified otherwise. Activation of Sol B was allowed to proceed for 20 minutes. After 2 and 3 hrs. additional EDC was added to Sol C (total EDC reported in ratio tables for individual lots).

TABLE 17

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 2-A | 45 | 19.3 | 0.8 | 34* |
| 2-B | 44 | 19.3 | 0.9 | 32* |
| 2-C | 44 | 19.9 | 1.4 | 37* |

*The corresponding process failed to provide products with the desired property.

The moderate binding of the synthesized graft co-polymers was not within the range of acceptable quantities for free ANP of 13% or less at 10% peptide loading. Thus, the ratio of reagents used for this process provided product that was inferior compared to the product produced by the process in the present disclosure.

TABLE 18

Ratios for Sample 2-A in Example 2

| Step | | Amount/value | Volume of solution |
|---|---|---|---|
| a | Amino in solution A (moles) | W = 0.536 mmol | Y = 4 mL |
| b | Carboxyl in solution B (moles) | 0.803 × W | Z = 7.3 mL |
| b | NHSS in solution B (moles) | 0.926 × W | Z = 7.3 mL |
| b | EDC in solution B (moles) | 1.61 × W | Z = 7.3 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 47.4 mM | |
| e | Additional EDC added to solution C [total EDC in C] (moles) | 1.94 × W [3.55 × W] | |
| f | Acetonitrile in Sol D | 20 mL | |
| g | DIPEA in solution D (moles) | 2.62 × W | |
| h | C18-NHS in solution E (moles) | 1.19 × W | Sol D volume + C18-NHS volume = 37.4 mL |

TABLE 19

Ratios for Sample 2-B in Example 2

| Step | | Amount/value | Volume of solution |
|---|---|---|---|
| a | Amino in solution A (moles) | W = 0.539 mmol | Y = 4 mL |
| b | Carboxyl in solution B (moles) | 0.799 × W | Z = 7.3 mL |
| b | NHSS in solution B (moles) | 0.921 × W | Z = 7.3 mL |
| b | EDC in solution B (moles) | 1.60 × W | Z = 7.3 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 47.7 mM | |
| e | Additional EDC added to solution C [total EDC in C] (moles) | 1.94 [3.54 × W] | |
| f | Acetonitrile in Sol D | 20 mL | |
| g | DIPEA in solution D (moles) | 2.61 × W | |
| h | C18-NHS in solution E (moles) | At least 1.18 × W | Sol D volume + C18-NHS volume = 37.4 mL |

TABLE 20

Ratios for Sample 2-C in Example 2

| Step | | Amount/value | Volume of solution |
|---|---|---|---|
| a | Amino in solution A (moles) | W = 0.548 mmol | Y = 4 mL |
| b | Carboxyl in solution B (moles) | 0.759 × W | Z = 7.1 mL |
| b | NHSS in solution B (moles) | 0.875 × W | Z = 7.1 mL |
| b | EDC in solution B (moles) | 1.52 × W | Z = 7.1 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 49.3 mM | |
| e | Additional EDC added to solution C [total EDC in C] (moles) | 1.92 × W [3.44 × W] | |
| f | Acetonitrile in Sol D | 20 mL | |
| g | DIPEA in solution D (moles) | 2.56 × W | |
| h | C18-NHS in solution E (moles) | 1.16 × W | Sol D volume + C18-NHS volume = 37.2 mL |

Example 3

Samples 3-A, 3-B, and 3-C

Synthesis of graft co-polymer 3-A, 3-B, and 3-C (5 kDa MPEG-CM; 20 kDa PL; 54, 60, and 56% saturation of primary amino groups with PEG and remaining primary amino groups modified with stearic acid) using MPEG-CM for the PEGylation reaction. The syntheses were performed as described in the General section unless specified otherwise. Activation of Sol B was allowed to proceed for 20 minutes. After 2 and 3 hrs additional EDC was added to Sol C (total EDC reported in ratio tables for individual lots).

TABLE 21

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 3-A | 54 | 18.0 | 1.1 | 24* |
| 3-B | 60 | 17.7 | 1.2 | 25* |
| 3-C | 56 | 18.8 | 1.3 | 22* |

*The corresponding process failed to provide products with the desired property.

The moderate binding of the synthesized graft co-polymers was not within the range of acceptable quantities for free ANP of 13% or less at 10% peptide loading. Thus, the ratio of reagents used for this process provided product that was inferior compared to the product produced by the process in the present disclosure.

TABLE 22

Ratios for Sample 3-A in Example 3

| Step | | Amount/value | Volume of solution |
|---|---|---|---|
| a | Amino in solution A (moles) | W = 0.536 mmol | Y = 4 mL |
| b | Carboxyl in solution B (moles) | 0.890 × W | Z = 7.9 mL |
| b | NHSS in solution B (moles) | 1.03 × W | Z = 7.9 mL |
| b | EDC in solution B (moles) | 1.79 × W | Z = 7.9 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 45.0 mM | |
| e | Additional EDC added to solution C [total EDC in C] (moles) | 2.13 × W [3.92 × W] | |
| f | Acetonitrile in Sol D | 20 mL | |
| g | DIPEA in solution D (moles) | 2.33 × W | |
| h | C18-NHS in solution E (moles) | 1.08 × W | Sol D volume + C18-NHS volume = 37.8 mL |

TABLE 23

Ratios for Sample 3-B in Example 3

| Step | | Amount/value | Volume of solution |
|---|---|---|---|
| a | Amino in solution A (moles) | W = 0.539 mmol | Y = 4 mL |
| b | Carboxyl in solution B (moles) | 0.885 × W | Z = 7.9 mL |
| b | NHSS in solution B (moles) | 1.02 × W | Z = 7.9 mL |
| b | EDC in solution B (moles) | 1.78 × W | Z = 7.9 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 45.3 mM | |
| e | Additional EDC added to solution C [total EDC in C] (moles) | 2.15 × W [3.92 × W] | |
| f | Acetonitrile in Sol D | 20 mL | |
| g | DIPEA in solution D (moles) | 2.32 × W | |
| h | C18-NHS in solution E (moles) | 1.07 × W | Sol D volume + C18-NHS volume = 37.8 mL |

TABLE 24

Ratios for Sample 3-C in Example 3

| Step | | Amount/value | Volume of solution |
|---|---|---|---|
| a | Amino in solution A (moles) | W = 0.548 mmol | Y = 4 mL |
| b | Carboxyl in solution B (moles) | 0.870 × W | Z = 7.9 mL |
| b | NHSS in solution B (moles) | 1.01 × W | Z = 7.9 mL |
| b | EDC in solution B (moles) | 1.75 × W | Z = 7.9 mL |
| b | pH of solution B | 4.0-5.5 | |
| b | Activation time (min) | 20 | |
| c & d | pH of solution C | 7.7 | |
| c & d | Amino in solution C (Molar) | W/(Y + Z) = 46.1 mM | |
| e | Additional EDC added to solution C [total EDC in C] (moles) | 2.11 × W [3.86 × W] | |
| f | Acetonitrile in Sol D | 20 mL | |
| g | DIPEA in solution D (moles) | 2.38 × W | |
| h | C18-NHS in solution E (moles) | 1.06 × W | Sol D volume + C18-NHS volume = 37.8 |

Example 4

Samples 4-A, 4-B, and 4-C

Synthesis of graft co-polymer 4-A, 4-B, and 4-C (5 kDa MPEG-CM; 20 kDa PL; 53, 51, and 47% saturation of primary amino groups with PEG and remaining primary amino groups modified with stearic acid) using MPEG-CM for the PEGylation reaction without preactivation. The syntheses were performed as described in the General section unless specified otherwise. Sol B was not prepared; reagents were added directly to Sol A.

TABLE 25

Properties of Synthesized Materials.

| Sample | % PEG Saturation | Hydrodynamic Diameter (nm) | Residual Amino (nmol/mg) | % Free ANP Evaluated at 10% Loading |
|---|---|---|---|---|
| 4-A | 53 | 22.9 | 0 | 21* |
| 4-B | 51 | 22.3 | 0 | 19* |
| 4-C | 47 | 22.9 | 0 | 16* |

*The corresponding process failed to provide products with the desired property.

The moderate binding of the synthesized graft co-polymers was not within the range of acceptable quantities for free ANP of 13% or less at 10% peptide loading. Thus, the ratio of reagents and method of addition used for this process provided product that was inferior compared to the product produced by the process in the present disclosure.

TABLE 26

Ratios for Sample 4-A in Example 4

| Step | | Amount/value | Volume of solution |
|---|---|---|---|
| a | Amino in solution A (moles) | W = 0.537 mmol | Y = 4 mL |
| b | Carboxyl in solution C (moles) | 0.839 × W | Z = 8 mL |
| b | NHSS in solution C (moles) | 0.995 × W | Z = 8 mL |
| b | EDC in solution C (moles) | 2.50 × W | Z = 8 mL |
| b | pH of solution B | not applicable | |
| b | Activation time (min) | 0 | |
| c & d | pH of solution C | 7.7 | |
| c & d | Amino in solution C (Molar) | W/(Y + Z) = 44.8 mM | |
| e | Additional EDC added to solution C [total EDC in C] (moles) | No additional EDC added | |
| f | Acetonitrile in Sol D | 21 mL | |
| g | DIPEA in solution D (moles) | 2.52 × W | |
| h | C18-NHS in solution E (moles) | 1.18 × W | Sol D volume + C18-NHS volume = 39.4 mL |

TABLE 27

Ratios for Sample 4-B in Example 4

| Step | | Amount/value | Volume of solution |
|---|---|---|---|
| a | Amino in solution A (moles) | W = 0.517 mmol | Y = 4 mL |
| b | Carboxyl in solution B (moles) | 0.870 × W | Z = 8 mL |
| b | NHSS in solution B (moles) | 1.06 × W | Z = 8 mL |
| b | EDC in solution B (moles) | 2.59 × W | Z = 8 mL |
| b | pH of solution B | not applicable | |
| b | Activation time (min) | 0 | |
| c & d | pH of solution C | 7.7 | |
| c & d | Amino in solution C (Molar) | W/(Y + Z) = 43.1 mM | |
| e | Additional EDC added to solution C [total EDC in C] (moles) | No additional EDC added | |
| f | Acetonitrile in Sol D | 21 mL | |
| g | DIPEA in solution D (moles) | 2.62 × W | |
| h | C18-NHS in solution E (moles) | 1.23 × W | Sol D volume + C18-NHS volume = 39.4 mL |

TABLE 28

Ratios for Sample 4-C in Example 4

| Step | | Amount/value | Volume of solution |
|---|---|---|---|
| a | Amino in solution A (moles) | W = 0.492 mmol | Y = 4 mL |
| b | Carboxyl in solution C (moles) | 0.914 × W | Z = 8 mL |
| b | NHSS in solution C (moles) | 1.09 × W | Z = 8 mL |
| b | EDC in solution C (moles) | 2.66 × W | Z = 8 mL |

TABLE 28-continued

Ratios for Sample 4-C in Example 4

| Step | | Amount/value | Volume of solution |
|---|---|---|---|
| b | pH of solution B | not applicable | |
| b | Activation time (min) | 0 | |
| c & d | pH of solution C | 7.7 | |
| c & d | Amino in solution C (Molar) | $W/(Y + Z) = 41.0$ mM | |
| e | Additional EDC added to solution C [total EDC in C] (moles) | No additional EDC added | |
| f | Acetonitrile in Sol D | 21 mL | |
| g | DIPEA in solution D (moles) | $2.75 \times W$ | |
| h | C18-NHS in solution E (moles) | $1.29 \times W$ | Sol D volume + C18-NHS volume = 39.4 mL |

Example 5

Samples 5-A, 5-B, and 5-C

Synthesis of graft co-polymer 5-A, 5-B, and 5-C (5 KDa MPEG-CM; 20 kDa PL; 57, 61, and 55% saturation of primary amino groups with PEG and remaining primary amino groups modified with stearic acid) using MPEG-CM for the PEGylation reaction without preactivation. The syntheses were performed as described in the General section unless specified otherwise. Sol B was not prepared; reagents were added directly to Sol A.

TABLE 29

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 5-A | 57 | 22.9 | 0 | 18* |
| 5-B | 61 | 22.3 | 0.1 | 17* |
| 5-C | 55 | 22.9 | 0.2 | 15* |

*The corresponding process failed to provide products with the desired property.

The moderate binding of the synthesized graft co-polymers were not within the range of acceptable quantities for free ANP of 13% or less at 10% peptide loading. Thus, the ratio of reagents and the method of addition used for this process provided product that was inferior compared to the product produced by the process in the present disclosure.

TABLE 30

Ratios for Sample 5-A in Example 5

| Step | | Amount/value | Volume of solution |
|---|---|---|---|
| a | Amino in solution A (moles) | W = 0.542 mmol | Y = 4 mL |
| b | Carboxyl in solution C (moles) | $0.821 \times W$ | Z = 8 mL |
| b | NHSS in solution C (moles) | $0.948 \times W$ | Z = 8 mL |
| b | EDC in solution C (moles) | $2.41 \times W$ | Z = 8 mL |
| b | pH of solution B | not applicable | |
| b | Activation time (min) | 0 | |
| c & d | pH of solution C | 7.7 | |
| c & d | Amino in solution C (Molar) | $W/(Y + Z) = 45.2$ mM | |
| e | Additional EDC added to solution C [total EDC in C] (moles) | No additional EDC added | |
| f | Acetonitrile in Sol D | 21.5 mL | |
| g | DIPEA in solution D (moles) | $2.50 \times W$ | |
| h | C18-NHS in solution E (moles) | $1.16 \times W$ | Sol D volume + C18-NHS volume = 39.9 mL |

TABLE 31

Ratios for Sample 5-B in Example 5

| Step | | Amount/value | Volume of solution |
|---|---|---|---|
| a | Amino in solution A (moles) | W = 0.601 mmol | Y = 4 mL |
| b | Carboxyl in solution C (moles) | $0.741 \times W$ | Z = 8 mL |
| b | NHSS in solution C (moles) | $0.849 \times W$ | Z = 8 mL |
| b | EDC in solution C (moles) | $2.20 \times W$ | Z = 8 mL |
| b | pH of solution B | not applicable | |
| b | Activation time (min) | 0 | |
| c & d | pH of solution C | 7.7 | |
| c & d | Amino in solution C (Molar) | $W/(Y + Z) = 50.1$ mM | |

TABLE 31-continued

Ratios for Sample 5-B in Example 5

| Step | | Amount/value | Volume of solution |
|---|---|---|---|
| e | Overall EDC added to solution C after 2 hours (moles), 2 more additions at 1 h intervals | No additional EDC added | |
| f | Acetonitrile in Sol D | 21.5 mL | |
| g | DIPEA in solution D (moles) | 2.25 × W | |
| h | C18-NHS in solution E (moles) | 1.04 × W | Sol D volume + C18-NHS volume = 39.9 mL |

TABLE 32

Ratios for Sample 5-C in Example 5

| Step | | Amount/value | Volume of solution |
|---|---|---|---|
| a | Amino in solution A (moles) | W = 0.604 mmol | Y = 4 mL |
| b | Carboxyl in solution C (moles) | 0.737 × W | Z = 8 mL |
| b | NHSS in solution C (moles) | 0.864 × W | Z = 8 mL |
| b | EDC in solution C (moles) | 2.19 × W | Z = 8 mL |
| b | pH of solution B | not applicable | |
| b | Activation time (min) | 0 | |
| c & d | pH of solution C | 7.7 | |
| c & d | Amino in solution C (Molar) | W/(Y + Z) = 50.3 mM | |
| e | Additional EDC added to solution C [total EDC in C] (moles) | No additional EDC added | |
| f | Acetonitrile in Sol D | 21.5 mL | |
| g | DIPEA in solution D (moles) | 2.24 × W | |
| h | C18-NHS in solution E (moles) | 1.04 × W | Sol D volume + C18-NHS volume = 39.9 mL |

Example 6

Samples 6-A, 6-B, and 6-C

Synthesis of graft co-polymer 6-A, 6-B, and 6-C (5 kDa MPEG-CM; 20 kDa PL; 99, 98, and 97% saturation of primary amino groups with PEG and remaining primary amino groups modified with stearic acid) using MPEG-CM for the PEGylation reaction without preactivation. The synthesis was performed as described in the General section unless specified otherwise. Sol B was not prepared; reagents were added directly to Sol A.

TABLE 33

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 6-A | 99 | 15.2 | 2.9 | 22* |
| 6-B | 98 | 14.7 | 3.7 | 27* |
| 6-C | 97 | 16.7 | 5.4 | 14* |

*The corresponding process failed to provide products with the desired property.

The moderate binding of the synthesized graft co-polymers was not within the range of acceptable quantities for free ANP of 13% or less at 10% peptide loading. The ratio of reagents used for the samples of experiment 6 was similar to the ratio of reagents used for graft co-polymer lots that produced acceptable binding characteristics (see, samples of experiments 7, 8, and 9), however only 6C was close to meeting ANP binding criteria. Additionally, the % PEG saturation was difficult to control due to precipitation and reached well above the 62% range described in the General procedure; the apparent saturation may be an artifact of precipitation as amino groups of PL would not be available for detection by TNBS if PL precipitated. Presumably preparation of Sol B (preactivation of PEG-SCM with NHSS and EDC in MES buffer at pH 4.0 to 5.5) is necessary for reproducibly preparing graft co-polymers with suitable binding characteristic. Thus, the process provided product that was inferior compared to the product produced by the process in the present disclosure although it is believed that acceptable product can be produced if the conditions leading to precipitation were avoided by adding powder reagents to solution A under vigorous stirring condition, a process that is different from failed Example 6 (Samples 6-A, 6-B, and 6-C).

TABLE 34

Ratios for Sample 6-A in Example 6

| Step | | Amount/value | Volume of solution |
|---|---|---|---|
| a | Amino in solution A (moles) | W = 0.566 mmol | Y = 4 mL |
| b | Carboxyl in solution C (moles) | 0.875 × W | Y + Z = 12 mL |
| b | NHSS in solution C (moles) | 2.64 × W | Y + Z = 12 mL |

TABLE 34-continued

Ratios for Sample 6-A in Example 6

| Step | | Amount/value | Volume of solution |
|---|---|---|---|
| b | EDC in solution C (moles) | 3.51 × W | Y + Z = 12 mL |
| b | pH of solution C | 7.7 | |
| b | Activation time (min) | 0 | |
| c & d | Amino in solution C (Molar) | W/(Y + Z) = 47.2 mM | |
| e | Additional EDC added to solution C [total EDC in C] (moles) | No additional EDC added | |
| f | Acetonitrile in Sol D | 22 mL | |
| g | DIPEA in solution D (moles) | 2.35 × W | |
| h | C18-NHS in solution E (moles) | 1.08 × W | Sol D volume + C18-NHS volume = 40.6 mL |

TABLE 35

Ratios for Sample 6-B in Example 6

| Step | | Amount/value | Volume of solution |
|---|---|---|---|
| a | Amino in solution A (moles) | W = 0.530 mmol | Y = 4 mL |
| b | Carboxyl in solution C (moles) | 0.934 × W | Y + Z = 12 mL |
| b | NHSS in solution C (moles) | 2.80 × W | Y + Z = 12 mL |
| b | EDC in solution C (moles) | 3.74 × W | Y + Z = 12 mL |
| b | pH of solution C | 7.7 | |
| b | Activation time (min) | 0 | |
| c & d | Amino in solution C (Molar) | W/(Y + Z) = 44.2 mM | |
| e | Additional EDC added to solution C [total EDC in C] (moles) | No additional EDC added | |
| f | Acetonitrile in Sol D | 22 mL | |
| g | DIPEA in solution D (moles) | 2.51 × W | |
| h | C18-NHS in solution E (moles) | 1.15 × W | Sol D volume + C18-NHS volume = 40.6 mL |

TABLE 36

Ratios for Sample 6-C in Example 6

| Step | | Amount/value | Volume of solution |
|---|---|---|---|
| a | Amino in solution A (moles) | W = 0.656 mmol | Y = 4 mL |
| b | Carboxyl in solution C (moles) | 0.754 × W | Y + Z = 12 mL |
| b | NHSS in solution C (moles) | 2.27 × W | Y + Z = 12 mL |
| b | EDC in solution C (moles) | 3.01 × W | Y + Z = 12 mL |
| b | Activation time (min) | 0 | |
| c & d | pH of solution C | 7.7 | |
| c & d | Amino in solution C (Molar) | W/(Y + Z) = 54.7 mM | |
| e | Additional EDC added to solution C [total EDC in C] (moles) | No additional EDC added | |
| f | Acetonitrile in Sol D | 22 mL | |
| g | DIPEA in solution D (moles) | 2.03 × W | |
| h | C18-NHS in solution E (moles) | 0.93 × W | Sol D volume + C18-NHS volume = 40.6 mL |

Example 7

Samples 7-A, 7-B, and 7-C

Synthesis of graft co-polymer 7-A, 7-B, and 7-C (5 kDa MPEG-CM; 20 kDa PL; 58, 55, and 55% saturation of primary amino groups with PEG and remaining primary amino groups modified with stearic acid) using MPEG-CM for the PEGylation reaction. The syntheses were performed as described in the General section unless specified otherwise. Activation of Sol B was allowed to proceed for 20 minutes. After 2 hours additional EDC was added to Sol C (total EDC reported in ratio tables for individual lots).

TABLE 37

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 7-A | 58 | 22.3 | 5.6 | 11* |
| 7-B | 55 | 23.0 | 13.9 | 12* |
| 7-C | 55 | 23.0 | 7.2 | 7* |

*The corresponding processes produce products that are efficient binders which is the desired property.

The synthesized graft co-polymers produced binding results of acceptable quantities for free ANP of 13% or lower at 10% peptide loading. Thus, the ratio of reagents used for the process in the present disclosure provided product that was acceptable.

TABLE 38

Ratios for Sample 7-A in Example 7

| Step | | Amount/value | Volume of solution |
|---|---|---|---|
| a | Amino in solution A (moles) | W = 0.545 mmol | Y = 4 mL |
| b | Carboxyl in solution B (moles) | 0.930 × W | Z = 8.5 mL |
| b | NHSS in solution B (moles) | 2.77 × W | Z = 8.5 mL |
| b | EDC in solution B (moles) | 2.80 × W | Z = 8.5 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 43.6 mM | |
| e | Additional EDC added to solution C [total EDC in C] (moles) | 0.94 × W [3.74 × W] | |
| f | Acetonitrile in Sol D | 22 mL | |
| g | DIPEA in solution D (moles) | 1.84 × W | |
| h | C18-NHS in solution E (moles) | 0.896 × W | Sol D volume + C18-NHS volume = 39.9 mL |

TABLE 39

Ratios for Sample 7-B in Example 7

| Step | | Amount/value | Volume of solution |
|---|---|---|---|
| a | Amino in solution A (moles) | W = 0.553 mmol | Y = 4 mL |
| b | Carboxyl in solution B (moles) | 0.916 × W | Z = 8.5 mL |
| b | NHSS in solution B (moles) | 2.73 × W | Z = 8.5 mL |
| b | EDC in solution B (moles) | 2.76 × W | Z = 8.5 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 44.1 mM | |
| e | Additional EDC added to solution C [total EDC in C] (moles) | 0.97 [3.73 × W] | |
| f | Acetonitrile in Sol D | 22 mL | |
| g | DIPEA in solution D (moles) | 2.07 × W | |
| h | C18-NHS in solution E (moles) | 0.949 × W | Sol D volume + C18-NHS volume = 39.9 mL |

TABLE 40

Ratios for Sample 7-C in Example 7

| Step | | Amount/value | Volume of solution |
|---|---|---|---|
| a | Amino in solution A (moles) | W = 0.544 mmol | Y = 4 mL |
| b | Carboxyl in solution B (moles) | 0.931 × W | Z = 8.5 mL |
| b | NHSS in solution B (moles) | 2.80 × W | Z = 8.5 mL |
| b | EDC in solution B (moles) | 2.51 × W | Z = 8.5 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 43.5 mM | |
| e | Additional EDC added to solution C [total EDC in C] (moles) | 1.07 × W [3.88 × W] | |
| f | Acetonitrile in Sol D | 22 mL | |
| g | DIPEA in solution D (moles) | 2.11 × W | |
| h | C18-NHS in solution E (moles) | 0.965 × W | Sol D volume + C18-NHS volume = 39.9 mL |

Example 8

Samples 8-A, 8-B, and 8-C

Synthesis of graft co-polymer 8-A, 8-B, and 8-C (5 KDa MPEG-CM; 20 kDa PL; 59, 51, and 41% saturation of primary amino groups with PEG and remaining primary amino groups modified with stearic acid) using MPEG-CM for the PEGylation reaction. The syntheses were performed as described in the General section unless specified otherwise. Activation of Sol B was allowed to proceed for 20 minutes. After 2 hours additional EDC was added to Sol C (total EDC reported in ratio tables for individual lots).

TABLE 41

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 8-A | 59 | 21.1+ | 3.1 | 8* |
| 8-B | 51 | 23.6 | 4.5 | 10* |
| 8-C | 41 | 24.2+ | 5.9 | 10* |

*The corresponding processes produce products that are efficient binder which is the desired property.

The synthesized graft co-polymers produced binding results of acceptable quantities for free ANP of 13% or less at 10% peptide loading. Thus, the ratio of reagents used for the process in the present disclosure provided product that was acceptable.

TABLE 42

Ratios for Sample 8-A in Example 8

| Step | | Amount/value | Volume of solution |
|---|---|---|---|
| a | Amino in solution A (moles) | W = 0.548 mmol | Y = 4 mL |
| b | Carboxyl in solution B (moles) | 0.886 × W | Z = 8.3 mL |
| b | NHSS in solution B (moles) | 2.67 × W | Z = 8.3 mL |
| b | EDC in solution B (moles) | 2.65 × W | Z = 8.3 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 43.6 mM | |
| e | Additional EDC added to solution C [total EDC in C] (moles) | 1.06 × W [3.71 × W] | |
| f | Acetonitrile in Sol D | 22 mL | |
| g | DIPEA in solution D (moles) | 2.44 × W | |
| h | C18-NHS in solution E (moles) | 1.12 × W | Sol D volume + C18-NHS volume = 44.6 mL |

TABLE 43

Ratios for Sample 8-B in Example 8

| Step | | Amount/value | Volume of solution |
|---|---|---|---|
| a | Amino in solution A (moles) | W = 0.534 mmol | Y = 4 mL |
| b | Carboxyl in solution B (moles) | 0.910 × W | Z = 8.3 mL |
| b | NHSS in solution B (moles) | 2.74 × W | Z = 8.3 mL |
| b | EDC in solution B (moles) | 2.72 × W | Z = 8.3 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 44.1 mM | |
| e | Additional EDC added to solution C [total EDC in C] (moles) | 0.98 × W [3.70 × W] | |
| f | Acetonitrile in Sol D | 22 mL | |
| g | DIPEA in solution D (moles) | 2.51 × W | |
| h | C18-NHS in solution E (moles) | 1.15 × W | Sol D volume + C18-NHS volume = 44.6 mL |

TABLE 44

Ratios for Sample 8-C in Example 8

| Step | | Amount/value | Volume of solution |
|---|---|---|---|
| a | Amino in solution A (moles) | W = 0.543 mmol | Y = 4 mL |
| b | Carboxyl in solution B (moles) | 0.894 × W | Z = 8.3 mL |
| b | NHSS in solution B (moles) | 2.69 × W | Z = 8.3 mL |
| b | EDC in solution B (moles) | 2.68 × W | Z = 8.3 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 43.5 mM | |
| e | Additional EDC added to solution C [total EDC in C] (moles) | 1.16 × W [3.84 × W] | |
| f | Acetonitrile in Sol D | 22 mL | |
| g | DIPEA in solution D (moles) | 2.48 × W | |
| h | C18-NHS in solution E (moles) | 1.13 × W | Sol D volume + C18-NHS volume = 44.7 mL |

Example 9

Samples 9-A, 9-B, 9-C, 9-D, 9-E, and 9-F

Synthesis of graft co-polymer 9-A, 9-B, 9-C, 9-D, 9-E, and 9-F (5 KDa MPEG-CM; 20 kDa PL; 62, 58, 55, 53, 56 and 56% saturation of primary amino groups with PEG and remaining primary amino groups modified with stearic acid) using MPEG-CM for the PEGylation reaction. The syntheses were performed as described in the General section unless specified otherwise. Activation of Sol B was allowed to proceed for 20 minutes. After 2 hours additional EDC was added to Sol C (total EDC reported in ratio tables for individual lots).

TABLE 45

Properties of Synthesized Materials

| Sample | % PEG Saturation | Hydrodynamic Diameter (nm) | Residual Amino (nmol/mg) | % Free ANP Evaluated at 10% Loading | Yield (g) |
|---|---|---|---|---|---|
| 9-A | 62 | 23.6 | 8.5 | 3* | 0.8 |
| 9-B | 58 | 23.6 | 6.6 | 4* | 0.8 |
| 9-C | 55 | 24.2 | 9.3 | 6* | 0.8 |
| 9-D | 53 | 22.3 | 5.8 | 1* | 5 |
| 9-E | 56 | 22.3 | 8.0 | 5* | 8 |
| 9-F | 56 | 21.7 | 5.4 | 3* | 42 |

*The corresponding processes produce products that are efficient binder which is the desired property The synthesized graft co-polymers produced binding results of acceptable quantities for free ANP of 13% or less at 10% peptide loading. Thus, the ratio of reagents used for the process in the present disclosure provided product that was acceptable.

TABLE 46

Ratios for Sample 9-A in Example 9

| Step | | Amount/value | Volume of solution |
|---|---|---|---|
| a | Amino in solution A (moles) | W = 0.559 mmol | Y = 4 mL |
| b | Carboxyl in solution B (moles) | 0.886 × W | Z = 8.4 mL |
| b | NHSS in solution B (moles) | 2.67 × W | Z = 8.4 mL |
| b | EDC in solution B (moles) | 2.66 × W | Z = 8.4 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 45.1 mM | |
| e | Additional EDC added to solution C [total EDC in C] (moles) | 0.89 × W [3.55 × W] | |
| f | Acetonitrile in Sol D | 22 mL | |
| g | DIPEA in solution D (moles) | 2.18 × W | |
| h | C18-NHS in solution E (moles) | 1.00 × W | Sol D volume + C18-NHS volume = 40.1 mL |

TABLE 47

Ratios for Sample 9-B in Example 9

| Step | | Amount/value | Volume of solution |
|---|---|---|---|
| a | Amino in solution A (moles) | W = 0.550 mmol | Y = 4 mL |
| b | Carboxyl in solution B (moles) | 0.900 × W | Z = 8.4 mL |
| b | NHSS in solution B (moles) | 2.71 × W | Z = 8.4 mL |
| b | EDC in solution B (moles) | 2.70 × W | Z = 8.4 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 44.4 mM | |
| e | Additional EDC added to solution C [total EDC in C] (moles) | 0.90 × W [3.60 × W] | |
| f | Acetonitrile in Sol D | 22 mL | |
| g | DIPEA in solution D (moles) | 2.22 × W | |
| h | C18-NHS in solution E (moles) | 1.02 × W | Sol D volume + C18-NHS volume = 40.1 mL |

TABLE 48

Ratios for Sample 9-C in Example 9

| Step | | Amount/value | Volume of solution |
|---|---|---|---|
| a | Amino in solution A (moles) | W = 0.542 mmol | Y = 4 mL |
| b | Carboxyl in solution B (moles) | 0.914 × W | Z = 8.4 mL |
| b | NHSS in solution B (moles) | 2.74 × W | Z = 8.4 mL |
| b | EDC in solution B (moles) | 2.74 × W | Z = 8.4 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 43.7 mM | |
| e | Additional EDC added to solution C [total EDC in C] (moles) | 0.92 × W [3.60 × W] | |
| f | Acetonitrile in Sol D | 22 mL | |
| g | DIPEA in solution D (moles) | 2.25 × W | |
| h | C18-NHS in solution E (moles) | 1.03 × W | Sol D volume + C18-NHS volume = 40.1 mL |

TABLE 49

Ratios for Sample 9-D in Example 9 (scale for 8 gram yield)

| Step | | Amount/value | Volume of solution |
|---|---|---|---|
| a | Amino in solution A (moles) | W = 4.6 mmol | Y = 35 mL |
| b | Carboxyl in solution B (moles) | 0.90 × W | Z = 70 mL |
| b | NHSS in solution B (moles) | 2.6 × W | Z = 70 mL |
| b | EDC in solution B (moles) | 2.7 × W | Z = 70 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 44 mM | |
| e | Additional EDC added to solution C [total EDC in C] (moles) | 0.92 × W [3.6W] | |
| f | Acetonitrile in Sol D | 186 mL | |
| g | DIPEA in solution D (moles) | 2.1 × W | |
| h | C18-NHS in solution E (moles) | 0.99 × W | Sol D volume + C18-NHS volume = 337 mL |

TABLE 50

Ratios for Sample 9-E in Example 9 (scale for 8 gram yield)

| Step | | Amount/value | Volume of solution |
|---|---|---|---|
| a | Amino in solution A (moles) | W = 4.5 mmol | Y = 35 mL |
| b | Carboxyl in solution B (moles) | 0.90 × W | Z = 70 mL |

TABLE 50-continued

Ratios for Sample 9-E in Example 9 (scale for 8 gram yield)

| Step | | Amount/value | Volume of solution |
|---|---|---|---|
| b | NHSS in solution B (moles) | 2.7 × W | Z = 70 mL |
| b | EDC in solution B (moles) | 2.8 × W | Z = 70 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 43 mM | |
| e | Additional EDC added to solution C [total EDC in C] (moles) | 0.90 × W [3.7W] | |
| f | Acetonitrile in Sol D | 188 mL | |
| g | DIPEA in solution D (moles) | 2.1 × W | |
| h | C18-NHS in solution E (moles) | 0.99 × W | Sol D volume + C18-NHS volume = 340 mL |

TABLE 51

Ratios for Sample 9-F in Example 9 (scale for 42 gram yield)

| Step | | Amount/value | Volume of solution |
|---|---|---|---|
| a | Amino in solution A (moles) | W = 24 mmol | Y = 175 mL |
| b | Carboxyl in solution B (moles) | 0.83 × W | Z = 335 mL |
| b | NHSS in solution B (moles) | 2.5 × W | Z = 335 mL |
| b | EDC in solution B (moles) | 2.7 × W | Z = 335 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 47 mM | |
| e | Additional EDC added to solution C [total EDC in C] (moles) | 0.70 × W [3.4W] | |
| f | Acetonitrile in Sol D | 900 mL | |
| g | DIPEA in solution D (moles) | 2.2 × W | |
| h | C18-NHS in solution E (moles) | 0.97 × W | Sol D volume + C18-NHS volume = 1650 mL |

Example 10

Samples 10-A, 10-B, and 10-C

Synthesis of graft co-polymer 10-A, 10-B, and 10-C (5 kDa MPEG-CM; 20 kDa PL; 49, 56 and 56% saturation of primary amino groups with PEG and remaining primary amino groups modified with stearic acid) using MPEG-CM for the PEGylation and extraction after PEGylation. The syntheses were performed as described in the General section unless specified otherwise. Activation of Sol B was allowed to proceed for 20 minutes. After 2, 3, and 4 hrs., additional EDC was added to Sol C (total EDC reported in ratio tables for individual lots). After the PEGylation reaction Sol C was extracted with a polar organic solvent (e.g., ethyl acetate) and Sol D was prepared from the aqueous phase of the extraction.

TABLE 52

Properties of Synthesized Materials

| Sample | % PEG Saturation | Hydrodynamic Diameter (nm) | Residual Amino (nmol/mg) | % Free ANP Evaluated at 10% Loading |
|---|---|---|---|---|
| 10-A | 49 | 22 | 4.8 | 55* |
| 10-B | 56 | 20 | 6.3 | 78* |
| 10-C | 56 | 20 | 6.3 | 72* |

*The corresponding process failed to provide products with the desired property.

The poor binding of the synthesized graft co-polymers were not within the range of acceptable quantities for free ANP of 13% or less at 10% peptide loading. The poor binding characteristics of the synthesized graft co-polymers can be attributed to disrupting the process by extracting Sol C with a polar organic solvent (e.g., ethyl acetate). This hypothesis is supported by comparing to similar processes (see, samples of experiments 1, 2, and 3) with the same ratio of reagents which produce graft co-polymers with moderate binding characteristics. Thus, the ratio of reagents used for this process and the disruption of the process with extraction of Sol C provided product that was inferior compared to the product produced by the process in the present disclosure.

TABLE 53

Ratios for Sample 10-A in Example 10

| Step | Amount/value | Volume of solution |
|---|---|---|
| a   Amino in solution A (moles) | W = 0.361 mmol | Y = 3 mL |
| b   Carboxyl in solution B (moles) | 0.809 × W | Z = 4.9 mL |
| b   NHSS in solution B (moles) | 0.920 × W | Z = 4.9 mL |
| b   EDC in solution B (moles) | 1.60 × W | Z = 4.9 mL |
| b   pH of solution B | 4.0-5.5 | |
| b   Activation time (min) | 20 | |
| c & d   pH of solution C | 7.7 | |
| c & d   Amino in solution C (Molar) | W/(Y + Z) = 45.7 mM | |
| e   Additional EDC added to solution C [total EDC in C] (moles) | 2.89 × W [4.49 × W] | |
| f   Acetone in Sol D | 70 mL | |
| g   DIPEA in solution D (moles) | 9.67 × W | |
| h   C18-NHS in solution E (moles) | 4.38 × W | Sol D volume + C18-NHS volume = 80 mL |

TABLE 54

Ratios for Sample 10-B in Example 10

| Step | Amount/value | Volume of solution |
|---|---|---|
| a   Amino in solution A (moles) | W = 0.361 mmol | Y = 3 mL |
| b   Carboxyl in solution B (moles) | 0.809 × W | Z = 4.9 mL |
| b   NHSS in solution B (moles) | 0.930 × W | Z = 4.9 mL |
| b   EDC in solution B (moles) | 1.60 × W | Z = 4.9 mL |
| b   pH of solution B | 4.0-5.5 | |
| b   Activation time (min) | 20 | |
| c & d   pH of solution C | 7.7 | |
| c & d   Amino in solution C (Molar) | W/(Y + Z) = 45.7 mM | |
| e   Additional EDC added to solution C [total EDC in C] (moles) | 2.89 × W [4.49 × W] | |
| f   Acetone in Sol D | 70 mL | |
| g   DIPEA in solution D (moles) | 9.67 × W | |
| h   C18-NHS in solution E (moles) | 4.40 × W | Sol D volume + C18-NHS volume = 80 mL |

TABLE 55

Ratios for Sample 10-C in Example 10

| Step | Amount/value | Volume of solution |
|---|---|---|
| a   Amino in solution A (moles) | W = 0.357 mmol | Y = 3 mL |
| b   Carboxyl in solution B (moles) | 0.818 × W | Z = 4.9 mL |
| b   NHSS in solution B (moles) | 0.930 × W | Z = 4.9 mL |
| b   EDC in solution B (moles) | 1.62 × W | Z = 4.9 mL |
| b   pH of solution B | 4.0-5.5 | |
| b   Activation time (min) | 20 | |
| c & d   pH of solution C | 7.7 | |
| c & d   Amino in solution C (Molar) | W/(Y + Z) = 45.2 mM | |
| e   Additional EDC added to solution C [total EDC in C] (moles) | 2.98 × W [4.60 × W] | |
| f   Acetone in Sol D | 70 mL | |
| g   DIPEA in solution D (moles) | 9.78 × W | |
| h   C18-NHS in solution E (moles) | 4.46 × W | Sol D volume + C18-NHS volume = 80 mL |

Example 11

Sample 11-A

Synthesis of graft co-polymer 11-A (5 kDa MPEG-CM; 20 kDa PL; 57% saturation of primary amino groups with PEG and remaining primary amino groups modified with stearic acid) using MPEG-CM for the PEGylation reaction and stopping the process before Fatylation. The synthesis was performed as described in the General section unless specified otherwise. Activation of Sol B was allowed to proceed for 20 minutes. Sol C was placed on ice at 1.75 hrs reaction time. At 2 hrs Sol C was returned to room temperature and additional EDC was added to Sol C (total EDC reported in ratio tables for individual lots). Sol C continued to react until a saturation of 57% of primary amino groups was reached at 3.75 hrs total time. Sol C was frozen and lyophilized. Sol D was prepared by dissolving the lyophilized material from Sol C into dichloromethane, and Sol D was not heated.

TABLE 56

Properties of Synthesized Material

| Sample | % PEG Saturation | Hydrodynamic Diameter (nm) | Residual Amino (nmol/mg) | % Free ANP Evaluated at 10% Loading |
|---|---|---|---|---|
| 11-A | 57 | 27.4 | 0 | 13* |

*The corresponding process failed to provide products with the desired property.

The moderate binding of the synthesized graft co-polymers was not within the range of acceptable quantities for free ANP of 13% or less at 10% peptide loading. The moderate characteristics of the synthesized graft co-polymers can be attributed to disrupting the process by lyophilization of Sol C. This hypothesis is supported by comparing to similar processes (see, samples of experiments 7, 8, and 9) with the same ratio of reagents which produce graft co-polymers with acceptable binding characteristics; note that the ratios of C18-NHS and DIPEA are not similar to the process of the present disclosure but that part of the process has a minimum requirement that all of the listed lots met. Thus, stopping the process by lyophilization of Sol C and not heating Sol D provided product that was inferior compared to the product produced by the process in the present disclosure.

TABLE 57

Ratios for Sample 11-A in Example 11

| Step | | Amount/value | Volume of solution |
|---|---|---|---|
| a | Amino in solution A (moles) | W = 2.66 mmol | Y = 23.5 mL |
| b | Carboxyl in solution B (moles) | 0.886 × W | Z = 40 mL |
| b | NHSS in solution B (moles) | 2.70 × W | Z = 40 mL |
| b | EDC in solution B (moles) | 2.66 × W | Z = 8.4 mL |
| b | pH of solution B | 4.0-5.5 | |
| b | Activation time (min) | 20 | |
| c & d | pH of solution C | 7.8 | |
| c & d | Amino in solution C (Molar) | W/(Y + Z) = 41.9 mM | |
| e | Additional EDC added to solution C [total EDC in C] (moles) | 0.91 × W [3.57 × W] | |
| f | Dichloromethane in Sol D | 75.5 mL | |
| g | DIPEA in solution D (moles) | 4.3 × W | |
| h | C18-NHS in solution E (moles) | 2.64 × W | Sol D volume + C18-NHS volume = 105 mL |

Example 12

Sample 12-A, PEG-SCM

Synthesis of graft co-polymer 12-A (5 kDa MPEG-SCM; 20 kDa PL; 53% saturation of amino groups with PEG and remaining amino groups modified with stearic acid) using MPEG-SCM for the PEGylation reaction. The synthesis was performed as described in the General section unless specified otherwise. The PL was dissolved in 50 mM Triethanolamine, pH 7.7. Sol B was not used as PEG-SCM was added directly to Sol A. Sol C was frozen after PEGylation. C18-NHS was dissolved in acetone.

TABLE 58

Properties of Synthesized Material

| Sample | % PEG Saturation | Hydrodynamic Diameter (nm) | Residual Amino (nmol/mg) | % Free ANP Evaluated at 10% Loading |
|---|---|---|---|---|
| 12-A | 53 | 18.2 | 0 | 100* |

*The corresponding process failed to provide products with the desired property.

The poor binding of the synthesized graft co-polymer was not within the range of acceptable quantities for free ANP of 13% or lower at 10% peptide loading. The exceptionally poor binding characteristics of the synthesized graft co-polymer can be attributed to the use of the PEG-SCM (NHS ester of 5 KDa PEG) reagent as opposed to preactivating PEG-CM with NHSS and EDC. This hypothesis is supported by comparing to different processes (see, sample 1-B, 4-A, and 9-C) that produce graft co-polymers with similar levels of PEG saturations and result in graft co-polymers with moderate to acceptable binding characteristics. Potentially, the PEG-SCM acylates PL at a different rate than the PEG-CM activated as an NHSS ester and affects PEG organization on PL which ultimately impacts the binding of ANP. Thus, the process which used PEG-SCM as a reagent for PEGylation provided product that was inferior compared to the product produced by the process in the present disclosure. No ANP binding was observed for graft co-polymers synthesized using NHS activation of MPEG-CM.

Evaluation of PGCs in Binding of GLP-1 and BNP Peptides

PGCs synthesized using the process of the present disclosure were also evaluated in their binding to GLP-1 and BNP, see table below. In addition to acceptable binding to ANP the PGCs also provided acceptable binding to both GLP-1 and BNP with 0-6% free peptide at 10% loading and 0% free peptide at 5% and 2% loading, respectively. This data supports that the process in the present disclosure is different and superior to the processes described in the previous publications (Castillo et al: showing 5% free at 2% loading for GLP-1). In addition, our data supports that the process in the present disclosure is different and superior to the processes described in the U.S. patent application Ser. No. 11/613,183 and U.S. patent application Ser. No. 11/971, 482 patent applications (showing 33% free at 10% loading for GLP-1).

TABLE 59

Binding Properties of Synthesized Material

| | % of free peptide (standard deviation) | | | | | | |
|---|---|---|---|---|---|---|---|
| | ANP | GLP-1 | | | BNP | | |
| Sample | 10% | 10% | 5% | 2% | 10% | 5% | 2% |
| 9-D | 0.84 (0.17) | 0 (0) | 0 (0) | 0 (0) | 4.06 (0.26) | 0 (0) | 0 (0) |
| 9-E | 5.34 (0.20) | 0 (0) | 0 (0) | 0 (0) | 5.46 (0.46) | 0 (0) | 0 (0) |
| 9-F | 3.29 (0.19) | 0 (0) | 0 (0) | 0 (0) | 5.86 (1.52) | 0 (0) | 0 (0) |

Two Step Process (EDC Quench, PL-PEG Isolation)

The synthesis of graft co-polymers can be accomplished by altering the process where the PEGylation reaction is stopped and the resulting PL-PEG product could be purified prior to the Fatylation reaction. This process would consist of preparing a series of solutions (Sol A, Sol B, Sol C, Sol D and Sol E) and combining them or by adding reagents to them during the PEGylation and Fatylation steps of the chemical process. Sol A would contain PL dissolved in buffer (HEPES or TEOA) and Sol B would contain mPEG-CM activated with NHSS and EDC in MES buffer. Sol C would be the reaction solution where PEGylation of PL occurs, prepared by combining Sol A and Sol B, or by adding reagents (NHSS, EDC or PEG-SCM) directly to Sol A, thus having zero minute preactivation or no Sol B. In some cases the chemical process does not require Sol B as in the case where PEG-SCM is added to Sol A to produce Sol C. Sol D would be prepared by adding organic solvent (acetonitrile, acetone or dichloromethane) to solution C and heating to 55-60° C. Then a strong nucleophile could be added to Sol D to quench remaining EDC. Acetonitrile in Sol D would be removed by aqueous/organic extraction (as in the general procedure for removal of acetonitrile after Fatylation). The aqueous phase containing PL-PEG product can then be diluted with water and purified via ultrafiltration. The purified PL-PEG product could then be used to make solution E by dissolving the product in 66% acetonitrile and heating to 55-60° C. after which C18-NHS, and DIPEA would be added.

Heating Sol D prior to quenching or stopping the PEGylation reaction is essential to preserve reaction rates similar to the process in the present disclosure and to produce product with acceptable binding characteristics. The processes used to synthesize PGC in examples 10 and 11 (see, samples 10-A, 10-B, 10-C, and 11-A) illustrate the poor outcome when the PEGylation reaction was stopped prior to the addition of organic solvent and heating; these processes resulted in PGCs that do not have acceptable binding. Thus, for a two-step procedure for PGC synthesis to be successful, heating Sol D prior to quenching the PEGylation reaction must be part of the process.

All of the patents and publications cited herein are hereby incorporated by reference in their entireties.

Those skilled in the art will recognize, or be able to ascertain using no more than routine experimentation, many equivalents to the specific embodiments of the disclosure described herein. Such equivalents are intended to be encompassed by the following claims. Unless otherwise indicated, the general mathematical rule of rounding off numbers applies to all the numbers in the present specification with the exception of molecular weight of a non-polydisperse molecule such as for example H2O, NHSS, EDC, etc. Polymers are poly-disperse molecules. Whenever a number is given, the last digit of the number is understood to be the limit of certainty and is a result of rounding off of the range of numbers to the nearest last digit of a given number. For example the "5 kDa polymer" means a range between 4.5 kDa to 5.5 kDa since rounding of 4.51-5.49 kDa to the nearest thousand is 5 kDa. Another example is 2.1 mmol is a range between of 2.05 to 2.15 mmol. Another example is 5.0 kDa polymer is a range between 4.95 to 5.05 kDa.

What is claimed:

1. A method of preparing a semi-random graft co-polymer, comprising:
    step (a): dissolving a linear polyamine backbone containing W moles of free primary amino groups in an aqueous solvent to provide solution A having a volume Y; and
    B1 or B2, wherein:
        B1 comprises steps (b), (c), (d), and (e):
            step (b): activating a protective chain selected from polyethylene glycol, polypropylene glycol, polyethylene-polypropylene glycol copolymer, methoxylated polyethylene glycol, methoxylated polypropylene glycol, methoxylated polyethylene-polypropylene glycol copolymer, ethoxylated polyethylene glycol, ethoxylated polypropylene glycol, and ethoxylated polyethylene-polypropylene glycol copolymer, wherein the protective chain contains 0.5-1.2×W moles of carboxyl groups with 1.7-7.0×W moles of N-hydroxysuccinimidesulfate and 1.5-3.6×W moles of 1-ethyl-3-[3-dimethylaminopropyl]carbodiimide hydrochloride in an aqueous solvent, at pH 4-5.5 having a final volume of Z, such that W/(Y+Z) has a ratio of 30-55 mM, for a period of time of up to 30 minutes to provide a solution B;
            step (c): adding solution B to solution A with continuous mixing to provide solution C;
            step (d): adjusting the pH of solution C to above 6.5; and
            step (e): adding 0.5-1.5×W of additional 1-ethyl-3-[3-dimethylaminopropyl]carbodiimide hydrochloride to solution C 2 to 3 hours after steps (b-d); and waiting until the primary amino groups are 55-40% of W moles to provide a semi-random graft co-polymer comprising a protective chain-grafted polyamine; and
        B2 comprises steps (b-d) and step (e):
            steps (b-d): adding a protective chain containing 0.5-1.2×W moles of carboxyl group, 1.7-7.0×W moles of N-hydroxysuccinimidesulfate, and 1.5-3.6×W moles of 1-ethyl-3-[3-dimethylaminopropyl]carbodiimide hydrochloride to solution A to provide solution C; adjusting the pH of solution C to above 6.5; and
            step (e): adding 0.5-1.5×W of additional 1-ethyl-3-[3-dimethylaminopropyl]carbodiimide hydrochloride to solution C 2 to 3 hours after steps (b-d); and waiting until the primary amino groups are 55-40% of W moles to provide a semi-random graft co-polymer comprising a protective chain-grafted polyamine.

2. The method of claim 1, wherein
    B1 and B2 each further comprises, after step (e):
        step (f): adding at least W moles of a strong nucleophile to solution C and purifying the semi-random graft co-polymer comprising the protective chain-grafted polyamine by ultrafiltration followed by lyophilization, and dissolving the immediate reaction product in acetonitrile to provide solution D, wherein the strong nucleophile comprises any one of hydroxyl amine, NaOR, LiR, NaOH, KOH, NaCCR, NaNH$_2$, NaNHR, NaNR$_2$, NaI, LiBr, KI, and NaN$_3$, wherein R is C$_1$-C$_6$ alkyl or C$_2$-C$_6$ alkenyl;
        step (g): adding 0.5-6×W moles of N,N-diisopropylethylamine or other tertiary amine to solution D; and
        step (h): adding at least 0.75×W moles of a long chain fatty acid-N-hydroxysuccinimide ester to solution D to provide solution E and stirring solution E at room temperature for at least 2 hours until the primary amino groups are less than 5% W moles to obtain a crude final product comprising a semi-random protective chain- and long fatty acid-grafted polyamine.

3. The method according to claim 2, further comprising steps:
    step (i): extracting the acetonitrile and any excess of long chain fatty acid-N-hydroxysuccinimide ester from the crude final product in solution E using ethyl acetate and discarding an ethyl acetate layer and repeating the extraction of a water layer at least once; and
    step (j): washing the water layer containing the final product by ultrafiltration by at least 10 volume changes of ethanol and water.

4. The method of claim 3, further comprising step (k) freezing the final product.

5. The method of claim 3, further comprising step (k) lyophilizing the final product.

6. A method according to claim 2, further comprising steps:

(i) exchanging an organic solvent in solution E containing the final product into water; and (j) washing the final product by ultrafiltration by at least 10 volume changes of ethanol and water.

7. A composition comprising a semi-random protective chain- and long fatty acid-grafted polyamine made according to the method of claim 2.

8. A pharmaceutical composition comprising a semi-random protective chain- and long fatty acid-grafted polyamine made according to the method of claim 2.

9. The method of claim 1, wherein
B1 and B2 each comprises, after step (e):
step (f) increasing total volume of solution C when the primary amino groups are 55-40% of W moles by adding 1.0-2.5 volume equivalent of acetonitrile to obtain solution D and heating solution D to 40-70° C. for at least 10 minutes, adding a strong nucleophile comprising any one of hydroxyl amine, NaOR, LiR, NaOH, KOH, NaCCR, $NaNH_2$, NaNHR, $NaNR_2$, NaI, LiBr, KI, and $NaN_3$, wherein R is $C_1$-$C_6$ alkyl or $C_2$-$C_6$ alkenyl; then purifying a resulting intermediate product by ultrafiltration and lyophilization to provide a pure intermediate product; and
reconstituting the pure intermediate product in 66% acetonitrile to provide a solution D;
step (g): after reconstituting the pure intermediate product to provide solution D, adding 0.5-6×W moles of N,N-diisopropylethylamine or other tertiary amine to solution D; and
step (h): after step (g), adding at least 0.75×W moles of long chain fatty acid N-hydroxysuccinimide ester in acetonitrile to provide solution E and stirring solution E at room temperature for at least 2 hours or until the primary amino groups are less than 5% of W moles to obtain a crude final product comprising a semi-random protective chain- and long fatty acid-grafted polyamine.

10. A composition comprising a semi-random protective chain and long fatty acid-grafted polyamine made according to the method of claim 9.

11. A pharmaceutical composition comprising a semi-random protective chain- and long fatty acid-grafted polyamine made according to the method of claim 9.

12. The method of claim 1, wherein
B1 and B2 each comprises, after step (e):
step (f): increasing total volume of solution C when the remaining primary amino groups is 55-40% of W moles by adding 1.0-2.5 volume equivalent of acetonitrile to obtain solution D and heating solution D to 40-70° C., inclusive;
step (g): adding 0.5-6×W N,N-diisopropylethylamine (DIPEA) or other tertiary amine to solution D; and
step (h): after step (g), adding at least 0.75×W equivalent of long chain fatty acid-N-hydroxysuccinimide ester (NHS) in acetonitrile to obtain solution E and stirring solution E at room temperature for at least 2 hours or until the remaining primary amino groups are less than 5% of W moles to obtain the crude final product comprising a semi-random protective chain- and long fatty acid-grafted polyamine,
wherein the linear polyamine backbone is polylysine with a degree of polymerization of 35-150, as determined by light scattering or nuclear magnetic resonance analysis; and
wherein the protective chain is methoxypolyethyleneglycol chain with a single carboxyl terminus and has a number average molecular weight of 4-12 kDa, as determined by gel permeation chromatography.

13. A composition comprising a semi-random protective chain- and long fatty acid-grafted polyamine made according to the method of claim 12.

14. A pharmaceutical composition comprising a semi-random protective chain- and long fatty acid-grafted polyamine made according to the method of claim 12.

15. The method of claim 1, wherein in B1, step (b) comprises activating the protective chain containing 0.5-1.1×W moles of carboxyl groups with 1.7-3.7×W moles of N-hydroxysuccinimidesulfate and 1.5-3.3×W moles of 1-ethyl-3-[3-dimethylaminopropyl]carbodiimide hydrochloride in an aqueous solvent; and
step (e) comprises adding 0.5-1.2×W moles of additional 1-ethyl-3-[3-dimethylaminopropyl]carbodiimide hydrochloride to solution C 2 to 3 hours after the pH adjustment in step (d); and
wherein in B2, steps (b-d) comprise adding the protective chain containing 0.5-1.1×W moles of carboxyl groups; 1.7-3.7×W moles of N-hydroxysuccinimidesulfate; and 1.5-3.3×W moles of 1-ethyl-3-[3-dimethylaminopropyl]carbodiimide hydrochloride to solution A to provide solution C; and
step (e) comprises adding 0.5-1.2×W moles of additional 1-ethyl-3-[3-dimethylaminopropyl]carbodiimide hydrochloride to solution C 2 to 3 hours after steps (b-d).

16. The method of claim 1, wherein in B1, step (b) comprises activating the protective chain containing 0.5-1.0×W moles of carboxyl groups with 1.7-3.4×W moles of N-hydroxysuccinimidesulfate and 1.5-3.0×W moles of 1-ethyl-3-[3-dimethylaminopropyl]carbodiimide hydrochloride in an aqueous solvent; and
step (e) comprises adding 0.5-1.1×W moles of additional 1-ethyl-3-[3-dimethylaminopropyl]carbodiimide hydrochloride to solution C 2 to 3 hours after the pH adjustment in step (d); and
wherein in B2, steps (b-d) comprise adding the protective chain containing 0.5-1.0×W moles of carboxyl groups; 1.7-3.4×W moles of N-hydroxysuccinimidesulfate; and 1.5-3.0×W moles of 1-ethyl-3-[3-dimethylaminopropyl]carbodiimide hydrochloride to solution A to provide solution C; and
step (e) comprises adding 0.5-1.1×W moles of additional 1-ethyl-3-[3-dimethylaminopropyl]carbodiimide hydrochloride to solution C 2 to 3 hours after steps (b-d).

* * * * *